US012680137B2

(12) United States Patent
Tan et al.

(10) Patent No.: US 12,680,137 B2
(45) Date of Patent: Jul. 14, 2026

(54) METHOD OF PREDICTING FOR BENEFIT FROM IMMUNE CHECKPOINT INHIBITION THERAPY

(71) Applicants: AGENCY FOR SCIENCE, TECHNOLOGY AND RESEARCH, Singapore (SG); NATIONAL UNIVERSITY HOSPITAL (SINGAPORE) PTE LTD, Singapore (SG); NATIONAL UNIVERSITY OF SINGAPORE, Singapore (SG)

(72) Inventors: Patrick Tan, Singapore (SG); Raghav Sundar, Singapore (SG); Kie Kyon Huang, Singapore (SG); Aditi Qamra, Singapore (SG); Jonathan Goke, Singapore (SG); Deniz Demircioglu, Singapore (SG)

(73) Assignees: AGENCY FOR SCIENCE, TECHNOLOGY AND RESEARCH, Sinagapore (SG); NATIONAL UNIVERSITY HOSPITAL (SINGAPORE) PTE LTD, Singapore (SG); NATIONAL UNIVERSITY OF SINGAPORE, Singapore (SG)

( * ) Notice: Subject to any disclaimer, the term of this patent is extended or adjusted under 35 U.S.C. 154(b) by 1361 days.

(21) Appl. No.: 17/416,903

(22) PCT Filed: Dec. 20, 2019

(86) PCT No.: PCT/SG2019/050629
§ 371 (c)(1),
(2) Date: Jun. 21, 2021

(87) PCT Pub. No.: WO2020/130948
PCT Pub. Date: Jun. 25, 2020

(65) Prior Publication Data
US 2022/0081723 A1     Mar. 17, 2022

(30) Foreign Application Priority Data
Dec. 21, 2018     (SG) ........................... 10201811546W

(51) Int. Cl.
*C12Q 1/6886* (2018.01)
*G16B 40/00* (2019.01)

(52) U.S. Cl.
CPC ........... *C12Q 1/6886* (2013.01); *G16B 40/00* (2019.02); *C12Q 2600/118* (2013.01); *C12Q 2600/158* (2013.01)

(58) Field of Classification Search
CPC ........... C12Q 1/6886; C12Q 2600/118; C12Q 2600/158; C12Q 2600/106; G16B 40/00; G16B 20/00; G16B 25/10; G16H 50/30; A61K 2039/507; A61K 39/395; C07K 16/2818; A61P 35/00; G01N 33/574; G01N 2800/52
See application file for complete search history.

(56) References Cited

U.S. PATENT DOCUMENTS

| | | | |
|---|---|---|---|
| 10,585,100 B2 | 3/2020 | Ogawa et al. | |
| 2016/0326597 A1 | 11/2016 | Chan et al. | |
| 2018/0251553 A1 | 9/2018 | McGranahan et al. | |
| 2019/0376146 A1 | 12/2019 | Yamada et al. | |

FOREIGN PATENT DOCUMENTS

| | | |
|---|---|---|
| JP | 2017-504324 A | 2/2017 |
| JP | 2018-527935 A | 9/2018 |
| WO | WO-2015/102536 A1 | 7/2015 |
| WO | WO-2016/044207 A1 | 3/2016 |
| WO | WO-2016/175275 A1 | 11/2016 |
| WO | WO-2016/196381 A1 | 12/2016 |
| WO | WO-2017/142484 A1 | 8/2017 |
| WO | WO-2018/097166 A1 | 5/2018 |

OTHER PUBLICATIONS

Kowanetz, Marcin, et al. "Differential regulation of PD-L1 expression by immune and tumor cells in NSCLC and the response to treatment with atezolizumab (anti-PD-L1)." Proceedings of the National Academy of Sciences 115.43 (2018) (Year: 2018).*
J. Couzin-Frankel, Breakthrough of the year 2013, "Cancer immunotherapy", *Science* 342, 2013, pp. 1432-1433.
Amarnath, et al., "The PDL1-PD1 axis converts human $T_H1$ cells into regulatory T cells", *Science translational medicine* 3, 111ra120, 2011, 14 pages.
Carbone et al., "First-Line Nivolumab in Stage IV or Recurrent Non-Small-Cell Lung Cancer", *N Engl J Med* 376, 2017, 18 pages.
Eng et al., "Atezolizumab with or without cobimetinib versus regorafenib in previously treated metastatic colorectal cancer (IMblaze370): a multicentre, open-label, phase 3, randomised, controlled trial", *The lancet oncology*, vol. 20, 2019, pp. 849-861.
Powles et al., "Atezolizumab versus chemotherapy in patients with platinum-treated locally advanced or metastatic urothelial carcinoma (IMvigor211): a multicentre, open-label, phase 3 randomised controlled trial", *Lancet* 391, 2018, pp. 748-757.

(Continued)

*Primary Examiner* — Soren Harward
*Assistant Examiner* — Dawn Bickham
(74) *Attorney, Agent, or Firm* — MARSHALL, GERSTEIN & BORUN LLP

(57) ABSTRACT

The present invention relates to a method of identifying a patient suffering from cancer as benefiting or not benefiting from immune checkpoint inhibition therapy comprising the steps of measuring an expression level of one or more preselected markers in a cancerous biological sample obtained from the patient, identifying a differentially expressed alternative promoter based on the expression level of the one or more preselected markers, calculating an alternative promoter usage score and identifying the patient as benefiting or not benefiting from immune checkpoint inhibition therapy using the alternative promoter usage score. The present invention also relates to a biomarker for excluding a patient suffering from cancer from immune checkpoint inhibition therapy.

5 Claims, 20 Drawing Sheets

(56) References Cited

OTHER PUBLICATIONS

J. S. J. Lim, R. Sundar, M. Chénard-Poirier, J. Lopez, T. A. Yap, "Emerging biomarkers for PD-1 pathway cancer therapy", *Biomarkers in Medicine*, 11(1), 2017, pp. 53-67.

Havel et al., "The evolving landscape of biomarkers for checkpoint inhibitor immunotherapy", *Nat Rev Cancer* 19, 2019, pp. 133-150.

Karapetis et al., K-ras mutations and benefit from cetuximab in advanced colorectal cancer:, *The New England journal of medicine* vol. 359, No. 17, Oct. 23, 2008, pp. 1757-1765.

Davuluri et al., "The functional consequences of alternative promoter use in mammalian genomes", *Trends in Genetica*, vol. 24, No. 4, 2008, pp. 167-177.

Bieberstein et al., "First exon length controls active chromatin signatures and transcription", *Cell Reports*, 2, Jul. 26, 2012, pp. 62-68.

Agarwal et al., "Use of alternative promoters to express the aromatase cytochrome P450 (CYP19) gene in breast adipose tissues of cancer-free and breast cancer patients", *The Journal of clinical endocrinology and metabolism*, vol. 81, No. 11, 1996, pp. 3843-3849.

Wiesner et al., "Alternative transcription initiation leads to expression of a novel ALK isoform in cancer", *Nature* 526, Oct. 15, 2015, pp. 453-457.

Qamra et al., "Epigenomic Promoter Alterations Amplify Gene Isoform and Immunogenic Diversity in Gastric Adenocarcinoma", *Cancer Discovery* 7, 2017, pp. 630-651.

Sundar et al., "Epigenomic promoter alterations predict for benefit from immune checkpoint inhibition in metastatic gastric cancer", *Ann Oncol* 30, 2019, pp. 424-430.

Demirciolu et al., "A Pan-Cancer Transcriptome Analysis Reveals Pervasive Regulation through Tumor-Associated Alternative Promoters", *bioRxiv*, 176487, 2018, 27 pages.

Rooney et al., "Molecular and genetic properties of tumors associated with local immune cytolytic activity", *Cell* 160, Jan. 15, 2015, pp. 48-61.

Thorsson et al., "The Immune Landscape of Cancer", *Immunity* 48, Apr. 17, 2018, pp. 812-830.

Yarchoan et al., "Tumor Mutational Burden and Response Rate to PD-1 Inhibition", *The New England journal of medicine* 377, Dec. 21, 2017, pp. 2500-2501.

Chiappinelli et al., "Combining Epigenetic and Immune Therapy to Combat Cancer", *Cancer research* 76, Apr. 1, 2016, pp. 1683-1689.

Brown et al., "Combining DNA damaging therapeutics with immunotherapy: more haste, less speed", *Br J Cancer* 118, 2018, pp. 312-324.

Fabregat et al., "The Reactome Pathway Knowledgebase", *Nucleic Acids Res*, vol. 44, 2016, pp. D481-D481.

Forrest et al., A promoter-level mammalian expression atlas. *Nature*, vol. 507, Mar. 27, 2014, pp. 462-470.

"An integrated encyclopedia of DNA elements in the human genome", *Nature*, 489, Sep. 6, 2012, pp. 57-74.

Bray et al., "Near-optimal probabilistic RNA-seq quantification", *Nat Biotechnol*, vol. 34, No. 5, May 2016, pp. 525-527.

Patro et al., "Salmon provides fast and bias-aware quantification of transcript expression", *Nature methods*, vol. 14, No. 4, Apr. 2017, 10 pages.

Mehnert et al., "Pembrolizumab for advanced papillary or follicular thyroid cancer: preliminary results from the phase 1b KEYNOTE-028 study", *Journal of Clinical Oncology* 34, 2016, pp. 6091-6091.

Mehnert et al., "Safety and antitumor activity of the anti-PD-1 antibody pembrolizumab in patients with advanced, PD-L1-positive papillary or follicular thyroid cancer", *BMC Cancer* 19, 196, 2019, 9 pages.

Giaccone et al., "Pembrolizumab in patients with thymic carcinoma: a single-arm, single-centre, phase 2 study", *Lancet Oncol*, vol. 19, Mar. 2018, 347-355.

Seto et al., "112O Primary result of an investigator-initiated phase II trial of nivolumab for unresectable or recurrent thymic carcinoma: PRIMER study (NCCH1505)", *Journal of Thoracic Oncology*, vol. 13, No. 4S, 2018, S61-S62.

Lopes et al., "Pembrolizumab (pembro) versus platinum-based chemotherapy (chemo) as first-line therapy for advanced/metastatic NSCLC with a PD-L1 tumor proportion score (TPS) ≥ 1%: Open-label, phase 3 KEYNOTE-042 study", *Journal of Clinical Oncology*, 36, 2018, 4 pages.

Carbone et al., "First-Line Nivolumab in Stage IV or Recurrent Non-Small-Cell Lung Cancer", *N Engl J Med*, 376, Jun. 22, 2017, pp. 2415-2426.

McDermott et al., "First-line pembrolizumab (pembro) monotherapy for advanced non-clear cell renal cell carcinoma (nccRCC): Results from KEYNOTE-427 cohort B", *Journal of Clinical Oncology* 37, 546-546 (2019.

Koshkin et al., "Clinical activity of nivolumab in patients with non-clear cell renal cell carcinoma", *J Immunother Cancer* 6, 9, 2018, 7 pages.

Burtness et al., "LBA8_PRKEYNOTE-048: Phase III study of first-line pembrolizumab (P) for recurrent/metastatic head and neck squamous cell carcinoma (R/M Hnscc)", *Annals of Oncology*, vol. 29, Supplement 8, Oct. 2018, 1 page.

Ferris et al., "Nivolumab for Recurrent Squamous-Cell Carcinoma of the Head and Neck", *N Engl J Med* 375, Nov. 10, 2016, pp. 1856-1867.

Ueno et al., "625PDPembrolizumab for advanced biliary adenocarcinoma: Results from the multicohort, phase II KEYNOTE-158 study", *Annals of Oncology*, vol. 29, Supplement 8, Oct. 2018, 1 page.

Kim et al., "A Phase 2 multi-institutional study of nivolumab for patients with advanced refractory biliary tract cancer", *JAMA Oncology*, 6(6), Jun. 2020, 15 pages.

Ott et al., Pembrolizumab in advanced endometrial cancer: Preliminary results from the phase lb KEYNOTE-028 study:, *Journal of Clinical Oncology* vol. 34, Issue 15, 2016, pp. 5581-5581.

McDermott et al., "Pembrolizumab monotherapy as first-line therapy in advanced clear cell renal cell carcinoma (accRCC): Results from cohort A of KEYNOTE-427", *Journal of Clinical Oncology*, vol. 36, Issue 15, 2018, pp. 4500-4500.

Motzer et al., "Nivolumab versus Everolimus in Advanced Renal Cell Carcinoma", *N Engl J Med*, vol. 373, Nov. 5, 2015, pp. 1803-1813.

Adams et al., "Pembrolizumab monotherapy for previously untreated, PD-L1-positive, metastatic triple-negative breast cancer: cohort B of the phase II KEYNOTE-086 study", *Ann Oncol*, 2019, 30, pp. 405-411.

Rugo et al., "Safety and Antitumor Activity of Pembrolizumab in Patients with Estrogen Receptor-Positive/Human Epidermal Growth Factor Receptor 2-Negative Advanced Breast Cancer", *Clin Cancer Res*, 24, Jun. 15, 2018, 2804-2811.

Higa et al., "Pembrolizumab for recurrent or advanced prostate cancer", Journal of Clinical Oncology, vol. 36, Issue 6, 2018, pp. 250-250.

Chung et al., "Pembrolizumab treatment of advanced cervical cancer: Updated results from the phase 2 KEYNOTE-158 study", *Journal of Clinical Oncology*, vol. 36, Issue 15, 2018, 3 pages.

Metaxas et al., "Pembrolizumab as Palliative Immunotherapy in Malignant Pleural Mesothelioma", *J Thorac Oncol*, vol. 13, No. 11, 2018, pp. 1784-1791.

Scherpereel et al., "Nivolumab or nivolumab plus ipilimumab in patients with relapsed malignant pleural mesothelioma (IFCT-1501 MAPS2): a multicentre, open-label, randomised, non- comparative, phase 2 trial", *Lancet Oncol*, 20, 2019, pp. 239-253.

Balar et al., "First-line pembrolizumab in cisplatin-ineligible patients with locally advanced and unresectable or metastatic urothelial cancer (KEYNOTE-052): a multicentre, single-arm, phase 2 study", *Lancet Oncol*, vol. 18, 2017, pp. 1483-1492.

Zhu et al., "Pembrolizumab in patients with advanced hepatocellular carcinoma previously treated with sorafenib (KEYNOTE-224): a non-randomised, open-label phase 2 trial", *Lancet Oncol*, vol. 19, 2018, pp. 940-952.

Le et al., "PD-1 Blockade in Tumors with Mismatch-Repair Deficiency", *N Engl J Med*, 372, Jun. 25, 2015, pp. 2509-2520.

Robert et al., "Pembrolizumab versus Ipilimumab in Advanced Melanoma", *N Engl J Med*, 372, Jun. 25, 2015, pp. 2521-2532.

(56) References Cited

OTHER PUBLICATIONS

Robert et al., "Nivolumab in previously untreated melanoma without BRAF mutation", *N Engl J Med*, 372, Jan. 22, 2015, pp. 320-330.

Fuchs et al., "KEYNOTE-059 cohort 1: Efficacy and safety of pembrolizumab (pembro) monotherapy in patients with previously treated advanced gastric cancer", *Journal of Clinical Oncology*, vol. 35, Issue 15, 2017, 5 pages.

Kang et al., "Nivolumab (ONO-4538/BMS-936558) as salvage treatment after second or later-line chemotherapy for advanced gastric or gastro-esophageal junction cancer (AGC): A double-blinded, randomized, phase III trial", *J Clin Oncol*, vol. 35, Issue 4, 2017, 4 pages.

Algazi et al., "Clinical outcomes in metastatic uveal melanoma treated with PD-1 and PD-L1 antibodies", *Cancer* 122, 2016, 29 pages.

Varga et al., "Pembrolizumab in patients with programmed death ligand 1-positive advanced ovarian cancer: Analysis of KEYNOTE-028", *Gynecol Oncol*, 152, 2019, pp. 243-250.

Hamanishi et al., "Safety and Antitumor Activity of Anti-PD-1 Antibody, Nivolumab, in Patients With Platinum-Resistant Ovarian Cancer", *Journal of Clinical Oncology*, vol. 33, Issue 34, 2015, 32 pages.

Tawbi et al., "Pembrolizumab in advanced soft-tissue sarcoma and bone sarcoma (SARC028): a multicentre, two-cohort, single-arm, open-label, phase 2 trial", *Lancet Oncol*, 18, 2017, pp. 1493-1501.

D'Angelo et al., "Nivolumab with or without ipilimumab treatment for metastatic sarcoma (Alliance A091401): two open-label, non-comparative, randomised, phase 2 trials", *Lancet Oncol*, 19, 2018, pp. 416-426.

Adra et al., "Phase II trial of pembrolizumab in patients with platinum refractory germ-cell tumors: a Hoosier Cancer Research Network Study GU14-206", *Ann Oncol*, 29, 2018, pp. 209-214.

Kojima et al., "Pembrolizumab versus chemotherapy as second-line therapy for advanced esophageal cancer: Phase III KEYNOTE-181 study", *Journal of Clinical Oncology*, vol. 37, Issue 4, 2019, 3 pages.

Reardon et al., ATIM-35. Results of the Phase IB KEYNOTE-028 Multi-Cohort Trial of Pembrolizumab Monotherapy in Patients With Recurrent PD-L1-POSITIVE Glioblastoma Multiforme (GBM). *Neuro-Oncology*, 18, 2016, vi25-vi26.

Omuro et al., "Nivolumab with or without ipilimumab in patients with recurrent glioblastoma: results from exploratory phase I cohorts of CheckMate 143", *Neuro Oncol*, 20, 2018, pp. 674-686.

Search Report and Written Opinion in International Application No. PCT/SG2019/050629 dated Mar. 4, 2020, 15 pages.

Communication Pursuant to Rules 70(2) and 70a(2) EPC, dated Sep. 23, 2022, 1 page.

Extended European Search Report in EP Application No. 19898711.7 dated Sep. 6, 2022, 11 pages.

Zappasodi et al., "Strategies for Predicting Response to Checkpoint Inhibitors", Current Hematologic Malignancy Reports, vol. 13, 2018, pp. 383-395.

Goltz et al., "*CTLA4* Methylation Predicts Response to Anti-PD-1 and Anti-CTLA-4 Immunotherapy in Melanoma Patients", JCI Insight, vol. 3, No. 13, Jul. 12, 2018, 10 pages.

Ayoubi et al., "Regulation of Gene Expression by Alternative Promoters", The FASEB Journal, vol. 10, No. 4, Mar. 1, 1996, pp. 453-460.

Duruisseaux et al., "Epigenetic Prediction of Response to Anti-PD-1 Treatment in Non-small-cell Lung Cancer: A Multicentre, Retrospective Analysis", The Lancet, Respiratory Medicine, vol. 6, No. 10, Oct. 1, 2018, pp. 771-781.

First Office Action in CN Application No. 201980092626.0 dated Dec. 13, 2023, 13 pages.

Written Opinion in SG Application No. 11202106708V dated Aug. 4, 2022, 15 pages.

Second Office Action, CN Application No. 201980092626.0, mailing date May 28, 2024, 12 pages.

Decision of Rejection in CN Application No. 201980092626.0, dated Dec. 13, 2024, 15 pages.

Second Office Action, Decision of Refusal, in JP Application No. 2021-536739 dated May 13, 2024, 16 pages.

Office Action, Notification of Reasons for Refusal, in JP Application No. 2021-536739 dated Dec. 11, 2023, 22 pages.

Communication Pursuant to Article 94(3) EPC in EP Application No. 19898711.7 dated Dec. 23, 2025, 5 pages.

Notice of Preliminary Rejection in KR Application No. 10-2021-7023202 dated May 30, 2025, 14 pages.

Qamra et al., "Epigenomic Promoter Alterations Amplify Gene Isoform and Immunogenic Diversity in Gastric Adenocarcinoma", Cancer Discovery, 7(6), Jun. 2017, pp. 630-651.

* cited by examiner

Alternative promoter usage score 2732 previously identified somatic alternative promoter sites 37 tumor samples Promoter activity estimation using RNA-Seq from TCGA PanCanAtlas

METHOD OF PREDICTING FOR BENEFIT FROM IMMUNE CHECKPOINT INHIBITION THERAPY

CROSS-REFERENCE TO RELATED APPLICATIONS

This application claims the benefit of priority of Singapore Application No. 10201811546W, filed 21 Dec. 2018, the contents of it being hereby incorporated by reference in its entirety for all purposes.

FIELD OF THE INVENTION

The present invention relates generally to the field of cancer. In particular, the present invention relates to the use of a method for selecting patients for immune checkpoint inhibition therapy.

BACKGROUND OF THE INVENTION

Among various treatment modalities for cancer, immune checkpoint inhibition (ICI) has made significant breakthroughs in several tumour types. In ICI therapy, immune checkpoint inhibitors such as pembrolizumab and nivolumab block interactions between the immune checkpoint receptor PD-1 and its ligands, reducing negative costimulatory signals and increasing T-effector cell function to elicit anti-tumour responses.

While beneficial in certain tumour types, several recent ICI phase III trials have also proved unsuccessful, particularly in solid epithelial tumours. Responses to ICI therapy are observed only in a minority of patients. Therefore, there is a need for robust biomarkers that can predict patient responses to immunotherapy. Currently, the most developed ICI biomarkers are PD-L1 expression, microsatellite instability, and tumour mutation burden. These biomarkers are positive predictive biomarkers aimed at identifying patients who will respond to ICI therapy. However, controversies surrounding these biomarkers have been raised and ICI responses in biomarker-negative populations have been observed. These observations highlight a complementary requirement for negative predictive biomarkers for ICI therapy, which can identify tumours that are likely to be resistant to immunotherapy. However, negative predictive biomarkers of ICI remain poorly described.

Promoters are genomic cis-regulatory elements upstream of transcription start sites (TSSs) which function to initiate transcription. Promoter activity is epigenetically regulated, and more than half of all human genes have multiple promoters, which can be selectively activated as a consequence of normal biological function or disease state. The use of alternative promoters can produce distinct 5' untranslated regions (UTRs) and first exons, enhancing mRNA and protein isoform diversity. In cancer, alternative promoters can generate cancer-specific isoforms with oncogenic properties. Recently, studies have demonstrated that tumours may utilize alternative promoters as a mechanism of immune-editing and evasion. Epigenetically-driven alternative promoter utilization is thus a potential mechanism of resistance to ICI therapy.

There is therefore a need to develop alternative methods based on alternative promoter utilization to predict patient response to immunotherapy or ICI therapy.

SUMMARY

In one aspect, there is provided a method of identifying a patient suffering from cancer as benefiting or not benefiting from immune checkpoint inhibition (ICI) therapy comprising the steps of:

a) measuring an expression level of one or more preselected markers in a cancerous biological sample obtained from the patient;

b) identifying a differentially expressed alternative promoter based on the expression level of the one or more preselected markers measured in step (a);

c) calculating an alternative promoter usage score;

d) identifying the patient as benefiting or not benefiting from ICI therapy using the alternative promoter usage score.

In another aspect, there is provided a method of determining the prognosis of a patient suffering from cancer comprising the steps of:

a) measuring an expression level of one or more preselected markers in a cancerous biological sample obtained from the patient;

b) identifying a differentially expressed alternative promoter based on the expression level of the one or more preselected markers measured in step (a);

c) calculating an alternative promoter usage score;

d) determining the prognosis of the patient using the alternative promoter usage score.

In another aspect, there is provided a biomarker for excluding a patient suffering from cancer from ICI therapy, wherein the biomarker is an alternative promoter usage score that is above the alternative promoter usage scores of one or more reference samples, wherein the alternative promoter usage score is the sum of the differentially expressed alternative promoters at each alternative promoter site.

Definitions

As used herein, the term "promoter" refers to a region of DNA that initiates transcription of a gene. A promoter may be a major promoter, a minor promoter or an alternative promoter. A major promoter is a promoter that is the most frequently used for the transcription of a gene.

As used herein, the terms "alternate promoter" and "alternative promoter" refer to a region of DNA that initiates transcription of a gene at an alternative transcription start site than the major promoter or the minor promoter.

The term "gained promoter" as used herein refers to a promoter that is gained or has increased activity in a cancerous biological sample compared to a non-cancerous biological sample. A gained promoter may be a promoter in the cancerous biological sample that is not present in the non-cancerous biological sample. A gained promoter may be a promoter in the cancerous biological sample that has an increased promoter activity compared to the promoter in the non-cancerous biological sample.

The term "lost promoter" as used herein refers to a promoter that is lost or has decreased activity in a cancerous biological sample compared to a non-cancerous biological sample. A lost promoter may be a promoter that is present in the non-cancerous biological sample but not in the cancerous biological sample. A lost promoter may be a promoter in the cancerous biological sample that has a decreased promoter activity compared to the promoter in the non-cancerous biological sample.

The term "immunotherapy" in the context of cancer refers to a form of therapy that involves the modulation of the immune system to treat cancer. Modulation of the immune system may involve the activation or inactivation of the immune system. This may involve the use of components of the immune system such as antibodies, cytokines and vaccines.

As used herein, the term "immune checkpoint inhibition therapy" refers to a form of cancer immunotherapy which targets key regulators of the immune system. Certain proteins made by some types of cancer cells and immune cells help keep immune responses in check and can keep T cells from killing cancer cells. Certain cancer cells use these proteins to evade immunosurveillance. The term "immune checkpoint inhibition therapy" refers to a therapy that involves the use of factors that block these proteins, restoring immune system function and allowing T cells to mount an effective antitumour response.

The term "prognosis", for the purposes of this application, refers to a prediction of the probable course and outcome of a clinical condition or disease. The term "prognosis" does not refer to the ability to predict the course or outcome of a condition with 100% accuracy. Instead, the term "prognosis" refers to the probability that a certain course or outcome will occur in a subject exhibiting a given condition, when compared to those individuals not exhibiting the condition. A "prognosis" can be made regarding one or more clinical outcomes, for example, the rate of progression of the disease in the subject, severity of the disease, survival rate, survival time, likelihood of metastasis, likelihood of disease recurrence or response to a therapeutic intervention.

The term "epigenetic", for the purposes of this application, refers to changes that regulate gene expression without altering an individual's DNA sequence. Examples of epigenetic alterations are DNA methylation, histone modifications and RNA-associated silencing. Epigenetic alterations play a vital role in disease development through control of gene expression.

The term "biomarker" in the context of this specification refers to a measurable indicator of a biological condition or disease. Biomarkers include but are not limited to substances, structures or processes that can be measured in body tissues and fluids.

As used herein, the terms "alternate promoter usage score" and "alternative promoter usage score" refer to a measure of alternative promoter utilization. The score can be expressed as an "AP" score or an "APB" score. The term "AP" in the context of $AP_{high}$ and $AP_{low}$ refers to alternate promoter utilization. An $AP_{high}$ score indicates a high alternative promoter utilization and an $AP_{low}$ score indicates a low alternative promoter utilization. The term "APB" in the context of $APB_{high}$ and $APB_{low}$ refers to alternate promoter utilization burden. An $APB_{high}$ score indicates a high alternative promoter utilization and an $APB_{low}$ score indicates a low alternative promoter utilization.

BRIEF DESCRIPTION OF THE DRAWINGS

The invention will be better understood with reference to the detailed description when considered in conjunction with the non-limiting examples and the accompanying drawings, in which.

Figure 1:
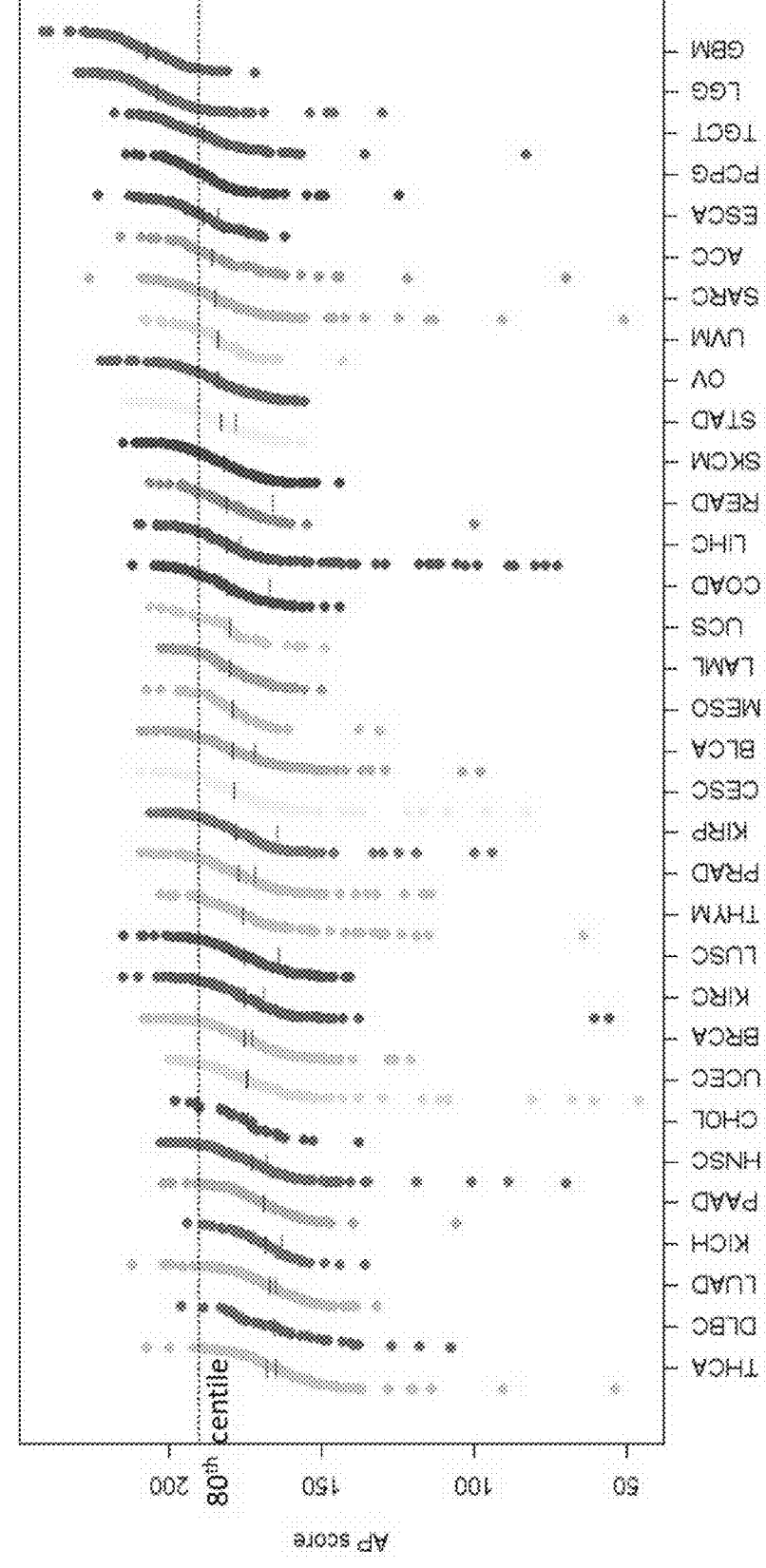
FIG. 1 shows the alternate promoter utilization burden (APBscore) across 33 tumour types. The APBscore was calculated in 10,393 samples across 33 tumour types. Each point represents the APBscore of a sample (y-axis). Tumour types are on the x-axis, ordered from lowest to highest median APBscore of the respective tumour type. The red horizontal bars are the median APBscore of the tumours, while the green horizontal bars represent the median APBscore of the corresponding normal tissue (provided only if at least 10 normal samples were available for analysis). The $80^{th}$ centile cut-off is shown as this was found to be the most ideal cut-point to dichotomize samples into the $APB_{high}$ and $APB_{low}$ groups.

The size of the circle corresponds to the number of patients treated in the clinical trial selected for ORR assessment. The color of the circle corresponds to the number of samples within the TCGA cohort used for assessment of APBscore. COAD includes both COAD and READ (colon and rectal cancer).

DETAILED DESCRIPTION OF THE PRESENT INVENTION

In a first aspect, the present invention refers to method of identifying a patient suffering from cancer as benefiting or not benefiting from immune checkpoint inhibition (ICI) therapy comprising the steps of:
  a) measuring an expression level of one or more preselected markers in a cancerous biological sample obtained from the patient;
  b) identifying a differentially expressed alternative promoter based on the expression level of the one or more preselected markers measured in step (a);
  c) calculating an alternative promoter usage score;
  d) identifying the patient as benefiting or not benefiting from ICI therapy using the alternative promoter usage score.

It will generally be understood to one of skill in the art that the cancerous biological sample may be a fresh, frozen, fixed or preserved sample.

In one embodiment, the patient suffering from cancer has undergone or is undergoing ICI therapy. In a preferred embodiment, the patient suffering from cancer has not undergone ICI therapy.

The cancerous biological sample may be taken from a patient diagnosed with one or more cancers which may include but are not limited to carcinoma, sarcoma and melanoma. The biological sample may be a cell, tissue or fluid sample.

In some embodiments, the cancerous biological sample may be taken from a patient suffering from one or more cancers which include but are not limited to adrenocortical carcinoma, bladder urothelial carcinoma, breast invasive carcinoma, cervical squamous cell carcinoma and endocervical adenocarcinoma, cholangiocarcinoma, colon adenocarcinoma, diffuse large B-cell lymphoma, esophageal carcinoma, glioblastoma multiforme, head and neck squamous cell carcinoma, kidney chromophobe, kidney renal clear cell carcinoma, kidney renal papillary cell carcinoma, acute myeloid leukaemia, brain lower grade glioma, liver hepatocellular carcinoma, lung adenocarcinoma, lung squamous cell carcinoma, mesothelioma, ovarian serous cystadenocarcinoma, pancreatic adenocarcinoma, pheochromocytoma and paraganglioma, prostate adenocarcinoma, rectum adenocarcinoma, sarcoma, skin cutaneous melanoma, stomach adenocarcinoma, testicular germ cell tumours, thyroid carcinoma, thymoma, uterine corpus endometrial carcinoma, uterine carcinosarcoma, uveal melanoma, anal carcinoma and combinations thereof.

In one embodiment, the cancer is a solid cancer. In another embodiment, the solid cancer is a gastro-intestinal cancer. In yet another embodiment, the gastro-intestinal cancer is a gastric cancer. In yet another embodiment, the gastric cancer is of the chromosomally unstable (CIN) and/or genomically stable (GS) subtype. In yet another embodiment, the gastric cancer is metastatic gastric cancer.

In some embodiments, the preselected marker is one or more nucleic acid molecules. The nucleic acid molecule may be a DNA or an RNA. In some embodiments, the nucleic acid molecule is selected from the group consisting of an mRNA, a cDNA, a microRNA and a genomic DNA. The preselected marker may be one or more genes or one or more transcripts. In some embodiments, the preselected marker is one or more peptides. In another embodiment, the peptide is a post-translationally modified peptide.

In one embodiment, the preselected marker is a marker that is associated with a somatic promoter region in a cancerous biological sample. In a preferred embodiment, the cancerous biological sample is a gastric cancer sample.

The expression level of the one or more preselected markers in the cancerous biological sample described herein may be measured using a method selected from the group consisting of whole transcriptome sequencing (WTS), Nanostring analysis, RNA sequencing, and combinations thereof.

It would be appreciated by a person skilled in the art that the usage of alternative promoters allows initiation of transcription at different transcription start sites. The usage of alternative promoters can therefore influence gene expression in various ways, including varying gene expression levels and/or causing the production of altered mRNA transcripts and protein isoforms.

In one embodiment, the differentially expressed alternative promoter described herein is identified by comparing the expression level of the one or more preselected markers in the cancerous biological sample with the expression level of the said one or more preselected markers in one or more reference samples to determine an increase or decrease in expression level of said preselected markers between the cancerous biological sample and the one or more reference samples. It will be understood to a person skilled in the art that the expression level of the preselected markers, which may be one or more genes, transcripts or peptides, may be regulated by the promoter and is therefore indicative of the activity of the promoter.

A differentially expressed alternative promoter may be identified by comparing the expression level of one or more preselected markers in the cancerous biological sample to the expression level of the one or more preselected markers in the one or more reference samples.

In one embodiment, an increase in the expression level of the one or more preselected markers in the cancerous biological sample compared to the expression level of the one or more preselected markers in the one or more reference samples for a gained promoter indicates a differentially expressed alternative promoter.

In another embodiment, a decrease in the expression level of the one or more preselected markers in the cancerous biological sample compared to the expression level of the one or more preselected markers in the one or more reference samples for a lost promoter indicates a differentially expressed alternative promoter.

The differentially expressed alternative promoter may be identified in various ways. In one embodiment, the differentially expressed alternative promoter described herein is identified by a gained promoter with an at least 4-fold increase in the expression level of transcripts when compared to the median expression level of transcripts for the promoter in a panel of tumour samples. In another embodiment, the differentially expressed alternative promoter described herein is identified by a lost promoter with an expression level of the transcripts which is less than 0.25-fold or at least a 4-fold reduction when compared to the median expression level of transcripts for the promoter in a panel of tumour samples. In one embodiment, the median expression level of transcripts for each promoter is the median expression level of the promoter across all samples in a panel of tumour samples.

In another embodiment, the differentially expressed alternative promoter described herein is identified by a gained promoter with a relative promoter activity greater than the median promoter activity of a panel of tumour samples. In another embodiment, the differentially expressed alternative promoter described herein is identified by a lost promoter with a relative promoter activity less than the median promoter activity of a panel of tumour samples. In one embodiment, the median expression level of transcripts for each promoter is the median expression level of the promoter across all samples in a panel of tumour samples.

In one embodiment, the gained promoter is a promoter that is gained or has increased activity in a cancerous biological sample compared to a non-cancerous biological sample. The gained promoter may be a promoter in the cancerous biological sample that is not present in the non-cancerous biological sample, or a promoter in the cancerous biological sample that has an increased promoter activity compared to the promoter in the non-cancerous biological sample.

In another embodiment, the lost promoter is a promoter that is lost or has decreased activity in a cancerous biological sample compared to a non-cancerous biological sample. A lost promoter may be a promoter that is present in the non-cancerous biological sample but not in the cancerous biological sample, or a promoter in the cancerous biological sample that has a decreased promoter activity compared to the promoter in the non-cancerous biological sample.

After the identification of differentially expressed alternative promoters as described herein, an alternative promoter usage score is then calculated. In one embodiment, the alternative promoter usage score may be an AP score. In another embodiment, the alternative promoter usage score may be an APBscore. The alternative promoter usage score may be calculated by determining the sum of the differentially expressed alternative promoters as described herein.

The alternative promoter usage score may be used in a method of identifying a patient suffering from cancer as benefiting or not benefiting from ICI therapy. The method of identifying a patient suffering from cancer as benefiting or not benefiting from ICI therapy may further comprise a step of comparing the alternative promoter usage score as described herein with a reference score to identify the patient as benefiting or not benefiting from ICI therapy.

In one embodiment, the reference score is a score at the median, tertile or quartile of alternative promoter usage scores from one or more reference samples. In another embodiment, the reference score is a score at the $10^{th}$, $20^{th}$, $30^{th}$, $40^{th}$, $50^{th}$, $60^{th}$, $70^{th}$, $80^{th}$ or $90^{th}$ percentile of alternative promoter usage scores from one or more reference samples. In a preferred embodiment, the reference score may be a score at the $66^{th}$ or $80^{th}$ percentile of alternative promoter usage scores from one or more reference samples.

In a preferred embodiment, the reference score is an absolute score. The absolute score is a fixed and non-variable score to which the patient's alternative promoter score is compared.

In one embodiment, an increased alternative promoter usage score compared to the reference score identifies the patient as not benefiting from ICI therapy. In one embodiment, the increased alternative promoter usage score is a score above the $66^{th}$ percentile of alternative promoter usage scores from one or more reference samples. In another embodiment, the increased alternative promoter usage score is a score above the $80^{th}$ percentile of alternative promoter usage scores from one or more reference samples.

In another embodiment, a decreased alternative promoter usage score compared to the reference score identifies the patient as benefiting from ICI therapy. In one embodiment, the decreased alternative promoter usage score is a score below the $66^{th}$ percentile of alternative promoter usages scores from one or more reference samples. In one embodiment, the decreased alternative promoter usage score is a score below the $80^{th}$ percentile of alternative promoter usages scores from one or more reference samples.

In one aspect, the present invention provides a method of determining the prognosis of a patient who is undergoing or has undergone ICI therapy, the method comprising the steps of:

a) measuring an expression level of one or more preselected markers in a cancerous biological sample obtained from the patient;

b) identifying a differentially expressed alternative promoter based on the expression level of the one or more preselected markers measured in step (a);

c) calculating an alternative promoter usage score;

d) determining the prognosis of the patient using the alternative promoter usage score.

In one embodiment, the method of determining the prognosis of a patient who is undergoing or has undergone ICI therapy as described herein further comprises the step of comparing the alternative promoter usage score described herein with a reference score to determine the prognosis of the patient, wherein an increased alternative promoter usage score compared to a reference score indicates a poorer prognosis.

In one embodiment, the increased alternative promoter usage score is a score above the $66^{th}$ percentile of alternative promoter usage scores from one or more reference samples. In another embodiment, the increased alternative promoter usage score is a score above the $80^{th}$ percentile of alternative promoter usage scores from one or more reference samples.

In another embodiment, the method of determining the prognosis of a patient who is undergoing or has undergone ICI therapy as described herein further comprises the step of comparing the alternative promoter usage score described herein with a reference score to determine the prognosis of the patient, wherein a decreased alternative promoter usage score compared to a reference score indicates a better prognosis.

In one embodiment, the decreased alternative promoter usage score is a score below the $66^{th}$ percentile of alternative promoter usages scores from one or more reference samples. In another embodiment, the decreased alternative promoter usage score is a score below the $80^{th}$ percentile of alternative promoter usages scores from one or more reference samples.

In another aspect, the present invention provides a biomarker for excluding a patient suffering from cancer from ICI therapy, wherein the biomarker is an alternative promoter usage score that is above the alternative promoter usage score of one or more reference samples, wherein the alternative promoter usage score is the sum of the differentially expressed alternative promoters at each alternative promoter site.

In one embodiment, the present invention provides a biomarker for excluding a patient suffering from cancer for ICI therapy, wherein the biomarker is an alternative promoter usage score that is above the $66^{th}$ percentile of alternative promoter usage scores of one or more reference samples, wherein the alternative promoter usage score is the sum of the differentially expressed alternative promoters at each alternative promoter site In another embodiment, the present invention provides a biomarker for selecting a patient suffering from cancer for ICI therapy, wherein the biomarker is an alternative promoter usage score that is below the $66^{th}$ percentile of alternative promoter usage scores of one or more reference samples, wherein the alternative promoter usage score is the sum of the differentially expressed alternative promoters at each alternative promoter site.

In another aspect, the present invention provides a biomarker for excluding a patient suffering from cancer from ICI therapy, wherein the biomarker is an alternative promoter usage score that is above the $80^{th}$ percentile of alternative promoter usage scores of one or more reference samples, wherein the alternative promoter usage score is the sum of the differentially expressed alternative promoters at each alternative promoter site.

In another embodiment, the present invention provides a biomarker for selecting a patient suffering from cancer for ICI therapy, wherein the biomarker is an alternative promoter usage score that is below the $80^{th}$ percentile of alternative promoter usage scores of one or more reference samples, wherein the alternative promoter usage score is the sum of the differentially expressed alternative promoters at each alternative promoter site.

The one or more reference samples may be selected from the group consisting of one or more tumour samples obtained from one or more different patients, one or more non-cancerous samples obtained from one or more different patients, one or more non-cancerous samples obtained from the same patient and combinations thereof. In one embodiment, the one or more non-cancerous samples obtained from the same patient is tissue adjacent to the cancerous tissue. It will be understood by the person skilled in the art that multiple combinations of these reference samples may be used in the methods of the invention.

In another aspect, the present invention refers to a method of determining if a patient suffering from cancer should not be treated with immune checkpoint inhibitor (ICI) therapy, the method comprising the steps of:

a) measuring an expression level of one or more preselected markers in a cancerous biological sample obtained from the patient;

b) identifying a differentially expressed alternative promoter based on the expression level of the one or more preselected markers measured in step (a);

c) calculating an alternative promoter usage score;

d) identifying the patient as not benefiting from ICI therapy using the alternative promoter usage score;

e) treating the patient with an alternative therapy when said patient is identified as not benefiting from ICI therapy.

In another aspect, the present invention refers to a method of treating a patient suffering from cancer, the method comprising the steps of:

a) measuring an expression level of one or more preselected markers in a cancerous biological sample obtained from the patient;

b) identifying a differentially expressed alternative promoter based on the expression level of the one or more preselected markers measured in step (a);

c) calculating an alternative promoter usage score;

d) identifying the patient as benefiting or not benefiting from ICI therapy using the alternative promoter usage score;

e) treating the patient identified as benefiting from ICI therapy according to step (d) with an immune check-point inhibitor, or treating the patient identified as not benefiting from ICI therapy according to step (d) with an alternative therapy.

In one embodiment, ICI therapy may include but is not limited to ipilimumab, nivolumab, pembrolizumab, atezolizumab, avelumab, durvalumab, cemiplimab, spartalizumab, sintilimab, camrelizumab and tislelizumab.

In another embodiment, the alterative therapy is any therapy other than ICI therapy that is suitable for treating cancer. For example, alternative therapies may include chemotherapy, radiation therapy, stem cell transplant, surgery, hormone therapy and targeted therapy. Targeted therapies involve the use of drugs that interfere with specific molecules necessary for tumour growth and progression. An alternative therapy may also include ceasing ICI therapy in a patient undergoing ICI therapy.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Non-limiting examples of the invention and comparative examples will be further described in greater detail by reference to specific Examples, which should not be construed as in any way limiting the scope of the invention.

Materials and Methods

REMARK criteria for validation of tumour biomarkers was followed in this study.
Clinical Cohorts
Discovery Cohort
Consecutive patients with metastatic gastric cancer treated with nivolumab or pembrolizumab treatment at Samsung Medical Centre, Seoul, Korea were included in this cohort. ICIs were administered as salvage treatment in patients who failed to at least one cytotoxic regimen. Nivolumab 3 mg/kg was administered as a 1-hour infusion every 2 weeks and Pembrolizumab 200 mg was administered as a 30-minute intravenous infusion every 3 weeks until disease progression or unacceptable toxicity. Ethics approval was obtained, and all patients provided written informed consent before archival tumour tissue specimens from primary tumours were collected and prospectively followed up for survival data.
Pembrolizumab Trial Cohort Patients with histologically proven metastatic and/or recurrent gastric adenocarcinoma that had failure of at least 1 line of chemotherapy that included platinum/fluoropyrimidine were enrolled in this study. The trial was conducted in accordance with the Declaration of Helsinki and the Guidelines for Good Clinical Practice (ClinicalTrials.gov identifier: NCT #02589496). The trial protocol was approved by the Institutional Review Board of Samsung Medical Center (Seoul, Korea) and all patients provided written informed consent before enrolment. Pembrolizumab 200 mg was administered as a 30-minute intravenous infusion every 3 weeks until documented disease progression, unacceptable toxicity, or up to 24 months. Tumour responses were evaluated every two cycles according to RECIST 1.1 criteria.
Nanostring Analysis NanoString nCounter Reporter CodeSets were designed for 80 recurrent somatic alternate promoter related genes, as well as immune-related genes corresponding to intra-tumoural cytolytic activity (CYT), cytokines and immune checkpoints. At least two probes were designed for each gene to measure the expression of canonical and alternate promoter-driven transcripts. A canonical probe at the 5' transcript marked by unaltered H3K4me3, and an alternate probe at the 5' transcript of the somatic promoter. Data analysis was performed using the vendor-provided nCounter software (nSolver). Raw counts were normalized using the geometric mean of the internal positive control probes included in each CodeSet.
RNA Sequencing Tumour tissues were obtained between day-42 and day 1 prior to initiation of study treatment. If tumour content was estimated as more than 40% after thorough pathological review, tumour DNA and RNA were extracted from freshly obtained tissues using a QIAamp Mini Kit (Qiagen, Hilden, Germany) according to the manufacturer's instructions. The concentrations and 260/280 and 260/230 nm ratios were measured with an ND1000 spectrophotometer (Nanodrop Technologies, Thermo-Fisher Scientific, MA, USA) and then further quantified DNA/RNA using a Qubit fluorometer (Life Technologies, CA, USA).
RNA Transcriptomic Analysis RNAseq data was aligned to GENCODE v19 transcript annotation using TopHat and FPKM abundance measure were generated using Cufflinks. Transcripts were then merged across all samples and normalized using Cuffnorm. To analyze alternative promoter-associated expression, RNAseq reads were mapped against the genomic location previously identified by epigenomic profiling. RNAseq mapping to these epigenome-defined promoter regions were then quantified, normalized by promoter length and by library size. Finally, fold changes in expression at each promoter site were computed between each tumour and the median expression level across all tumour samples.

PDL1 immunohistochemistry analysis, MSI status, EBV status, TCGA subtyping and tumour mutational burden were based on classifications used for a phase II study of single agent pembrolizumab in metastatic gastric cancer.

Statistical Analysis

Associations of clinicopathologic features to histologic sub-classification was performed using Fisher's Exact Test. Progression-free survival (PFS) was calculated from the time of first dose of pembrolizumab to the time of disease progression or death, and overall survival (OS) was calculated from time of first dose of pembrolizumab or nivolumab to time of death. Kaplan-Meier (KM) curves and log rank test were used for survival analysis. The hazard ratio (HR) and its 95% confidence interval (CI) were evaluated for each analysis using Cox proportional hazards regression model. All analyses were done using R (3.4.1). In the validation cohort, samples with alternate promoter usage score greater than the $66^{th}$ percentile were defined as high alternate promoter utilization ($AP_{high}$) and remaining as low alternate promoter utilization ($AP_{low}$).

PDL1 Immunochemistry

PDL1 immunhistochemisty was performed using the Dako PD-L1 IHC 22C3 pharmDx kit (Agilent Technologies). PD-L1 protein expression was determined using CPS, which was the number of PD-L1 staining cells (tumour cells, lymphocytes, macrophages) divided by the total number of viable tumour cells, multiplied by 100.

MSI Status

Tumour tissue MSI status was determined by both IHC for MLH1 and MSH2 and PCR analysis of 5 markers with mononucleotide repeats.

EBV Status Subtypes

EBV status was determined by EBV-encoded small RNA (EBER) in situ hybridization.

Tumour Mutational Burden

Mutational load was determined from whole exome sequencing analysis. Mutational load for a subject was defined as the number of somatic non-synonymous SNVs that passed all filters. Somatic mutations were annotated with variant effect predictors. Mutational load was calculated as the number of non-synonymous SNVs in the tumour exome data. The ML-H threshold for tissue was set as the upper tertile.

TGCA Subtype Definition

Gastric cancer subtypes defined by TCGA was based on DNA genomic alterations. These groups included EBV(+), MSI-H, CIN and genome stable tumours, which lack CIN and are heavily enriched in the diffuse histologic subtype. As a proxy for CIN, EBV(−), MSS tumours were stratified into CIN and genome stable based on their TP53 status. Mutational signature analysis was performed using the deconstructSigs package (v1.6.0) in R.

Dataset

Promoter activity was inferred from RNA-Seq data available from the PanCanAtlas of the TCGA consisting of 10393 samples (9668 tumour and 725 normal samples) across 33 tumour types.

APBscore Algorithm

The initial epigenetic promoter alteration study in gastric cancer identified 2732 somatic promoter regions (2053 gained and 679 lost) and transcriptomic expression of these isoforms were used to create the APBscore algorithm.

For the TCGA data, GENCODE v19 annotation was used to determine the set of promoters. The overlapping first exons of each TSS were combined to obtain a set of promoters. Activity of each promoter was then quantified using junction reads aligning into the first introns of the constituting transcripts. The total junction read counts were then normalized across the entire dataset. The $log_2$ transformed normalized read counts were used for promoter activity in further downstream analysis. Gene expression estimates were obtained by summing up the activities of each promoter per gene. Each promoter's activity was then normalized by gene expression to obtain relative promoter activities. In total 113,076 promoters were identified.

Somatic promoter regions identified in gastric cancer were then selected from this set of 113,076 promoters. 4672 promoters (3263 in gained region, 1409 in lost regions) were located within the 2732 somatic promoter regions identified in gastric cancer. Of these 4672 promoters, the median relative promoter activity of every promoter across all tumour samples (n=9668) was calculated. For every sample, the APBscore was calculated as the number of gained promoters with relative promoter activity greater than median and lost promoters with relative promoter activity less than median (FIG. 1). APBscore at various centile cut-offs ($10^{th}$, $20^{th}$, $30^{th}$ . . . , $90^{th}$) were used to dichotomize tumours into $APB_{high}$ and $APB_{low}$. The $80^{th}$ centile was determined as the ideal cut-off for the $APB_{high}$ and $APB_{low}$ groups and used for further downstream analysis. Normal samples were only added into the cohort for the analyses involving normal tissue and were not used in the calculation of median scores and cut-offs.

Immune Correlates

Transcriptomic expression levels of CD8A, GZMA and PRF1 and a selection of more than 700 genes including immune checkpoints, markers of various immune cell types, genes related to the adaptive and innate immune response and antigens was selected and extracted from the TCGA dataset from the Broad GDAC Firehose.Immune subtypes, other immune signatures and TMB were extracted from a Pan-Cancer immune landscape analysis. Progression-free survival (PFS) and overall survival (OS) including censorship data was extracted from the Pan-Cancer immune landscape analysis.

Immune Checkpoint Inhibitor Clinical Data

Data from clinical trials involving immune checkpoint inhibitors is rapidly expanding, with drugs being tested as single agent and in combination with other therapies. Pembrolizumab remains the immune checkpoint inhibitor that has been tested across the broadest spectrum of tumour types with clinical trial data being reported. Therefore, an extensive literature review of single agent pembrolizumab trials was conducted and the largest studies that were reported for each tumour type were selected. Objective response rates (ORR) from these trials were then correlated with APBscores of each tumour type. TMB was extracted from the Pan-Cancer immune landscape analysis and PD-L1 transcript expression was extracted from the Broad GDAC Firehose.

Statistical Analysis

Wilcoxon rank-sum test was used to compare expression levels of CD8A, GZMA and PRF1 between $APB_{high}$ and $APB_{low}$ groups. The "Rtsne" R package was used to generate T-SNE plots. Pearson's test was used for correlation between APBscore and ORR of pembrolizumab. Kaplan-Meier (KM) curves and log rank test were used for survival analysis. The hazard ratio (HR) and its 95% confidence interval (CI) were evaluated for each analysis using Cox proportional hazards regression model. Network mapping of somatic promoter gene function was done using the Reactome Pathway Database. All analyses were done using R (3.5.2).

Validation of Estimation of Promoter Activity Using RNA-Seq

The accuracy of promoter activity estimation using RNA-Seq was validated by bench-marking against other "gold-standard" measures such as H3K4me3 ChIP-Seq and CAGE tag data available on public data-sets. H3K4me3 levels correlated strongly with RNA-Seq promoter activity, suggesting that epigenetic-based and transcript-based estimates of promoter activity were consistent (Kruskal-Wallis p<0.001). The findings were confirmed with CAGE-Tag data, with unique promoters identified on RNA-Seq having higher CAGE-Tag support.

The present algorithm was also compared with other bioinformatic methods utilized in RNA-Seq quantification and first exon read counts. The present algorithm yielded results similar to these algorithms with high levels of correlation (Pearson's correlation coefficient >0.85). Overall, this analysis demonstrates that our approach enables the quantitative, robust, and reproducible estimation of promoter activity from RNA-Seq data.

Example 1: Alternate Promoter Utilization in Metastatic Gastric Cancer

Figure 2A:
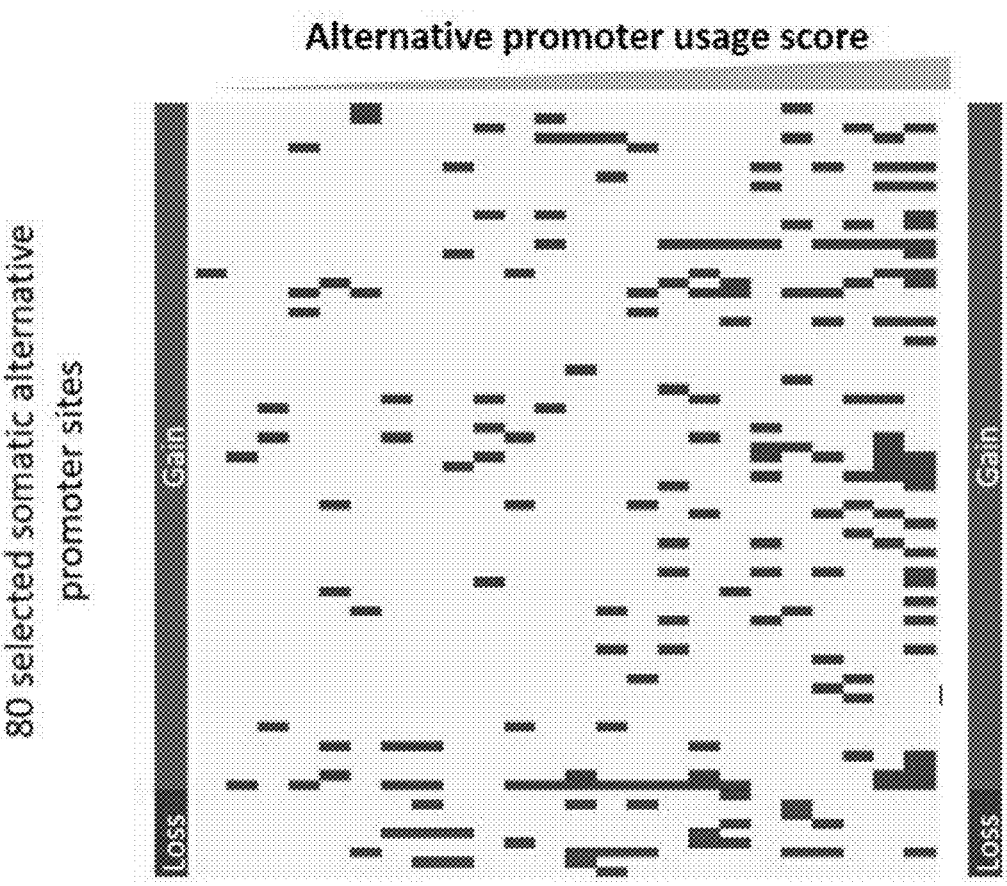
FIG. 2 shows the alternate promoter utilization in gastric cancer (discovery cohort, n=24). In particular, (A) shows a heatmap of alternate promoter utilization in discovery cohort of patients treated with nivolumab or pembrolizumab. Transcript with higher than 4-fold expression level compared to the median level in all tumour and mapping to the previously identified gain alternative promoter site were considered as gained alternative promoter (marked in light grey, in the upper portion "Gain"). Transcript with lower than 4-fold expression level compared to the median level in all tumour and mapping to the previously identified lost alternative promoter site were considered as lost alternative promoter (marked in dark grey, in the lower portion "Loss"). (B) shows the association between $AP_{high(disc)}$ group vs $AP_{low(disc)}$ group with T-cell immune correlates. $AP_{high(disc)}$ group are in light grey, whereas those in $AP_{low(disc)}$ group are in dark grey. Depicted are the expression of T-cell markers CD8A (P=0.059) and the T-cell cytolytic markers GZMA (P=0.025) and PRF1 (P=0.011). $AP_{high(disc)}$ group shows lower expression of immune markers. (C) shows a Kaplan Meier curve of progression free survival comparing $AP_{high}$ group vs $AP_{low}$ group in the discovery cohort.

The first cohort consisted of 24 metastatic gastric cancer patients treated with nivolumab and pembrolizumab (29 subjects were initially included, with 24 tumour samples passing quality control for sufficient tissue for Nanostring analysis). A customized Nanostring panel was used to measure transcripts associated with either the canonical or alternate promoter. Differentially expressed alternative promoters were defined as a promoter site showing <0.25× fold change (for lost somatic promoters) or >4× fold change in expression level (for gained somatic promoters) over the median across all samples. Using this algorithm, it was found that a third of the tumours (8/24) displayed high alternate promoter utilization in more than 10% of the sites (>8/80). This group was defined as $AP_{high}$ while the rest were defined as $AP_{low}$ (FIG. 2A).

Figure 2B:
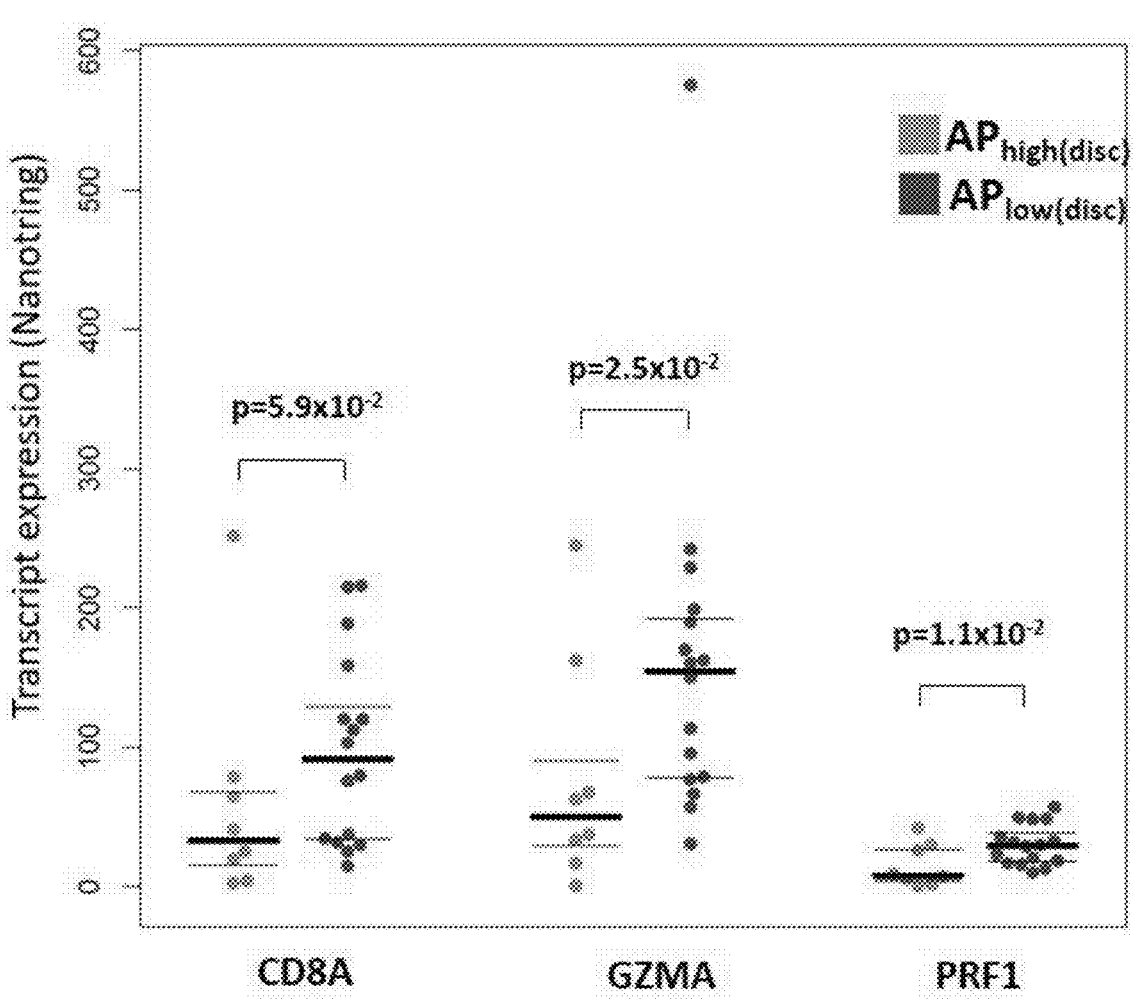
Figure 2C:
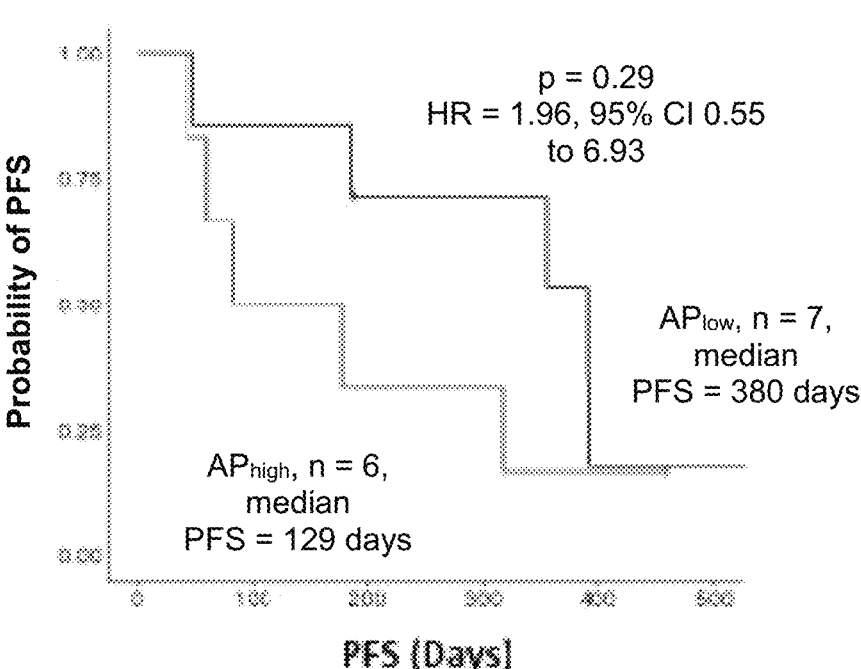

Measurement of cytolytic T-cell activity had previously been described by studying expression of CD8A (CD8+ tumour infiltrating lymphocytes), granzyme A (GZMA) and perforin 1 (PRF1). The $AP_{low}$ group demonstrated significantly increased expression of GZMA (P=0.025), PRF1 (P=0.011) and CD8A (P=0.059) when compared to the $AP_{high}$ group suggesting increased cytotoxic T-cell activity in the $AP_{low}$ group (FIG. 2B). These findings are concordant with earlier results described in early gastric cancer, demonstrating that alternate promoter utilization in metastatic gastric cancers is also inversely related to anti-tumour immunity. Notably, despite the small sample size, heterogenous treatment regimens, and non-trial based nature of this cohort, there was a trend for patients with $AP_{high}$ tumours to have worse progression-free survival (PFS) compared to patients with $AP_{low}$ tumours (129 days vs 389 days, HR 1.96 95% CI: 0.55 to 6.93, P=0.29, FIG. 2C). Based on these findings, this hypothesis was further tested in a separate cohort of uniformly-treated patients.

Figure 3A:
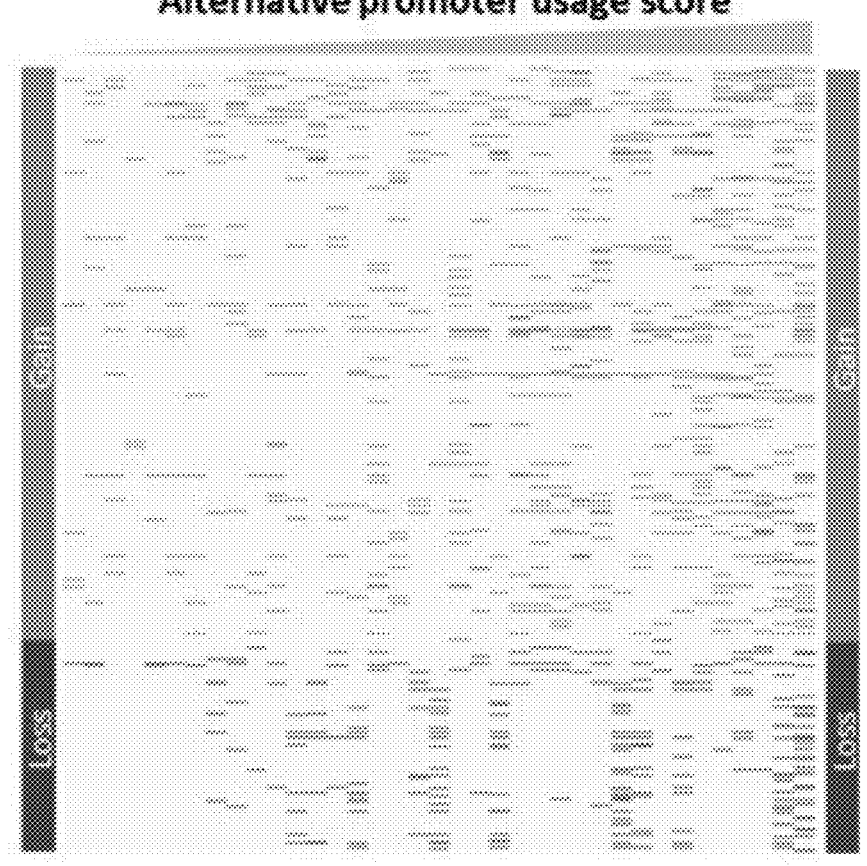
FIG. 3 shows the alternate promoter utilization in gastric cancer (pembrolizumab trial cohort, n=37). In particular, (A) shows a heatmap of alternate promoter utilization. Transcript with higher than 4-fold expression level compared to the median level in all tumour and mapping to the previously identified gain alternative promoter site were considered as gained alternative promoter (marked in light grey, in the upper portion "Gain"). Transcript with lower than 0.25-fold expression level compared to the median level in all tumour and mapping to the previously identified lost alternative promoter site were considered as lost alternative promoter (marked in dark grey, in the lower portion "Loss"). (B) shows a graph of alternative promoter utilization scores. Alternative promoter utilization score is calculated as the sum of gained and lost alternative promoter in each sample. High alternate promoter utilization was defined as those >$66^{th}$ centile. (C) shows the association between $AP_{high}$ group vs $AP_{low}$ group with T-cell immune correlates. $AP_{high}$ group are in light grey, whereas those in $AP_{low}$ group are in dark grey. Depicted are the expression of T-cell markers CD8A (P=0.0037) and the T-cell cytolytic markers GZMA (P=0.0055) and PRF1 (P=0.016). $AP_{high}$ group shows lower expression of immune markers. (D) is a waterfall plot of response to pembrolizumab according to $AP_{high}$ (light grey) and $AP_{low}$ (dark grey) subgroups. Y axis represents percentage of maximum tumour reduction assessed according to RECIST 1.1 criteria.
Figure 3B:
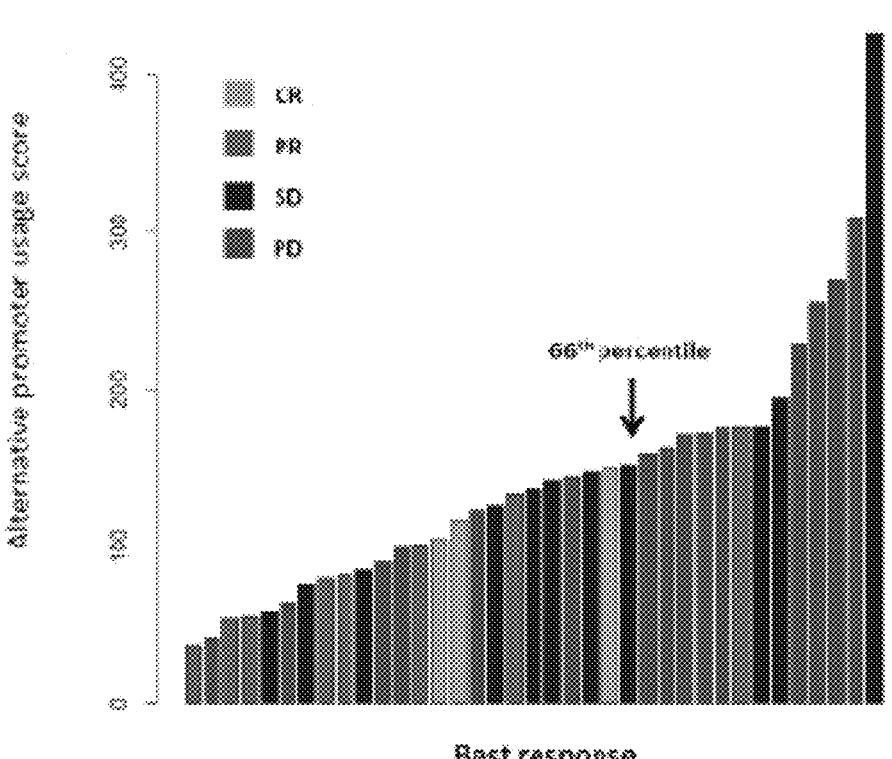

Example 2: Alternate Promoter Utilization as a Predictor of Response and Survival with Pembrolizumab Treatment For the second cohort, transcriptomic data from the phase II study described earlier was used. Transcriptomic data from pretreatment biopsy samples and matched clinical data was available for 37 subjects and used for analysis. The median age was 57 years, 73% were male (N=27), 4 (11%) were EBV positive and 4 were MSI (11%) with the rest defined as CIN or GS TCGA subtype. Complete or partial responses to therapy was seen in 11 subjects (30%). Using 2732 somatic alternate promoter sites previously identified in gastric cancer [10], differentially expressed alternative promoters were defined similar to the first cohort (<0.25× fold change for known somatically lost promoters or >4× fold change for known somatically gained promoters). Notably, good concordance between RNAseq and Nanostring platforms for assessment of alternate promoter utilization has previously been shown. The sum of differentially expressed sites in each sample was calculated to define an alternate promoter usage score (FIG. 3A). Scores ranged from 37 to 426 (median 136) (FIG. 3B). Using data from the first cohort to guide cut-off points, the $AP_{high}$ group was defined as samples >66% centile (n=13), while $AP_{low}$ constituted the remaining samples.

Figure 3C:
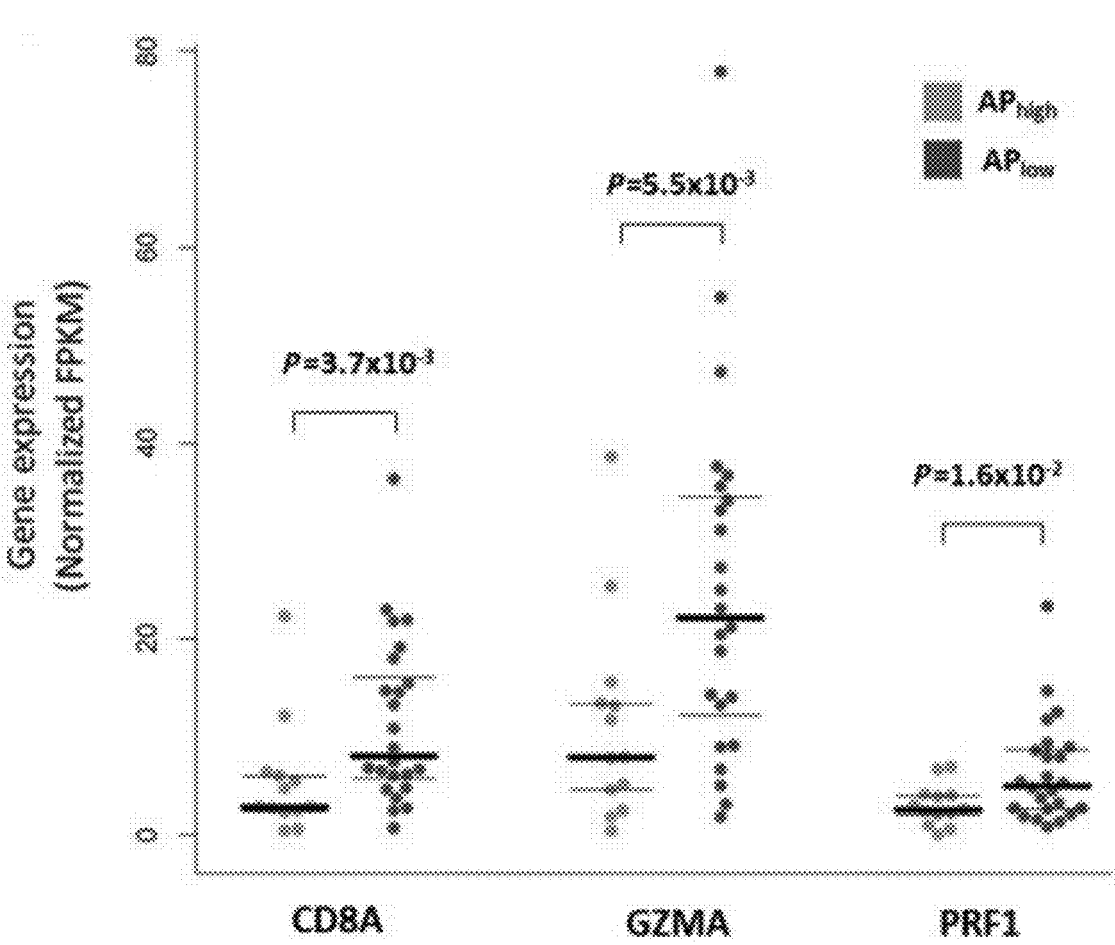
Figure 3D:
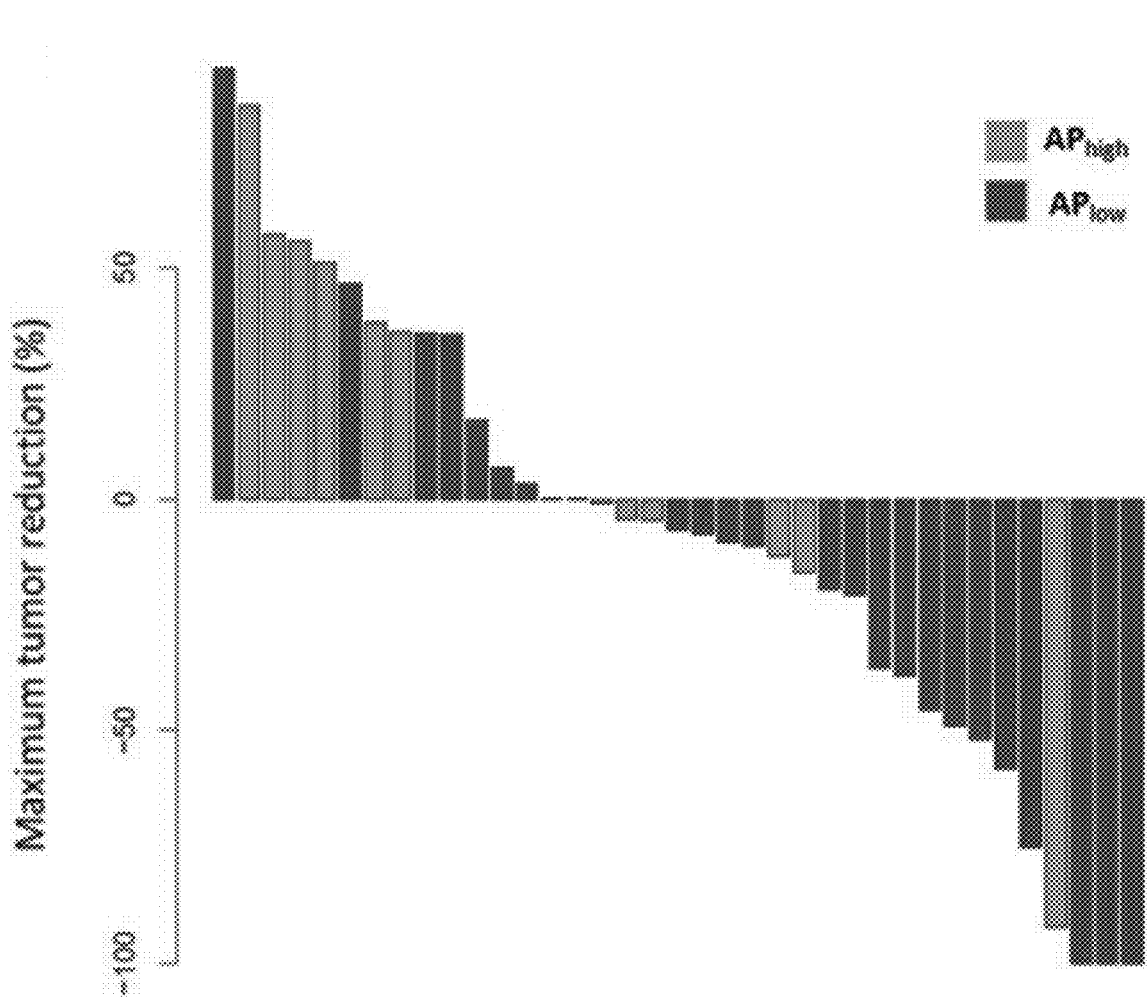
Figure 4A:
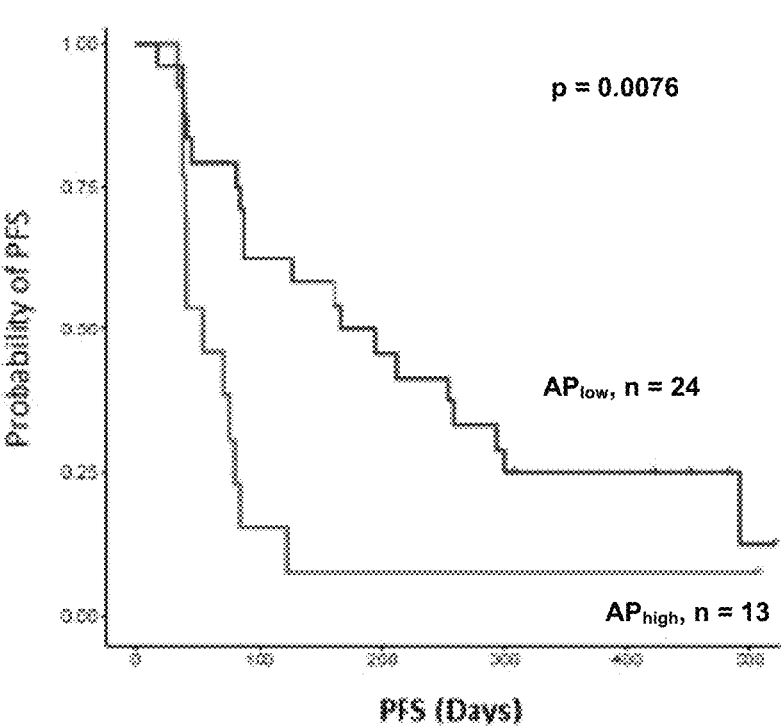
FIG. 4 shows the survival curves based on alternate promoter utilization. In particular, (A) shows a Kaplan Meier curve of progression free survival comparing $AP_{high}$ group vs $AP_{low}$ group. (B) shows a Swimmer plot where the x-axis represents the duration of pembrolizumab therapy for each patient. $AP_{high}$ (light grey) and $AP_{low}$ (dark grey) subgroups are depicted. (C) shows a Kaplan Meier curve of progression free survival comparing TCGA subtypes split by $AP_{high}$ group vs $AP_{low}$ group.
Figure 4B:
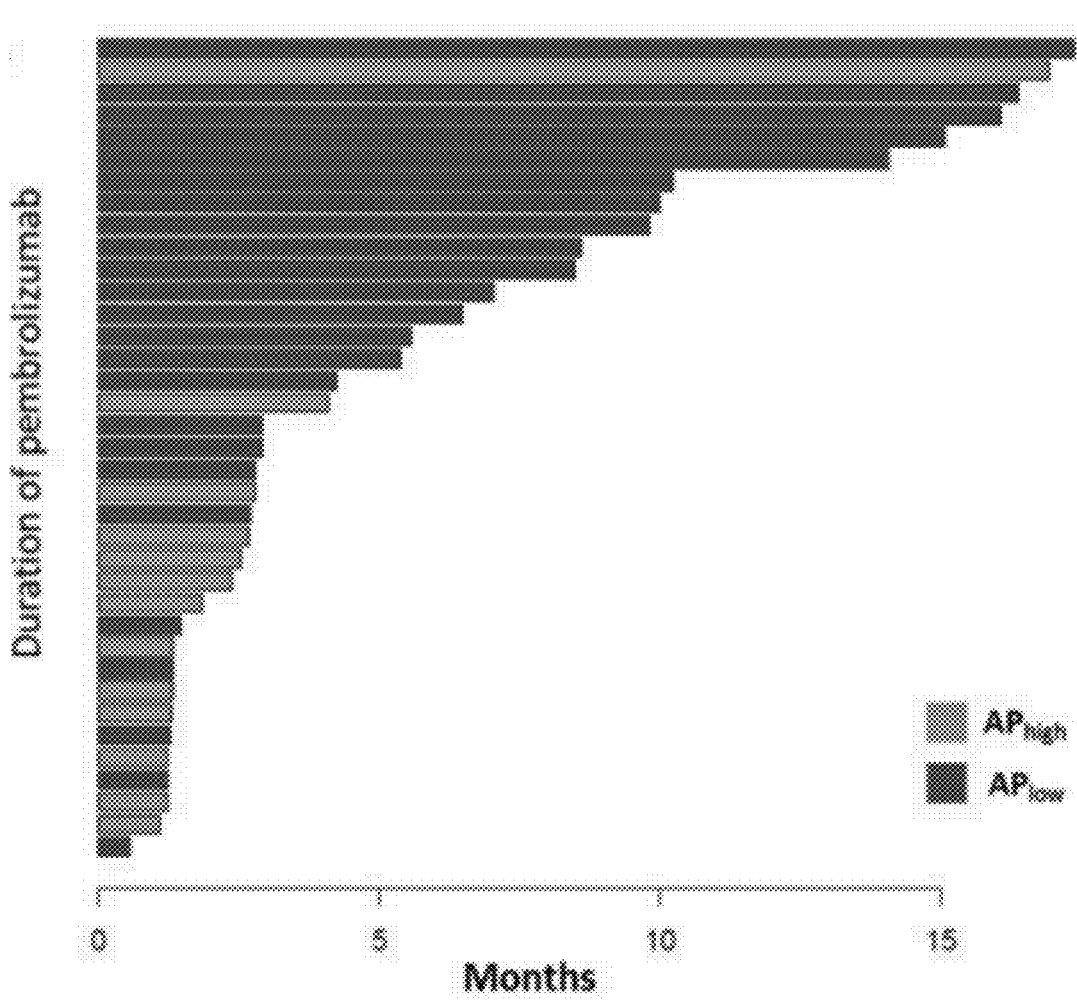
Figure 4C:
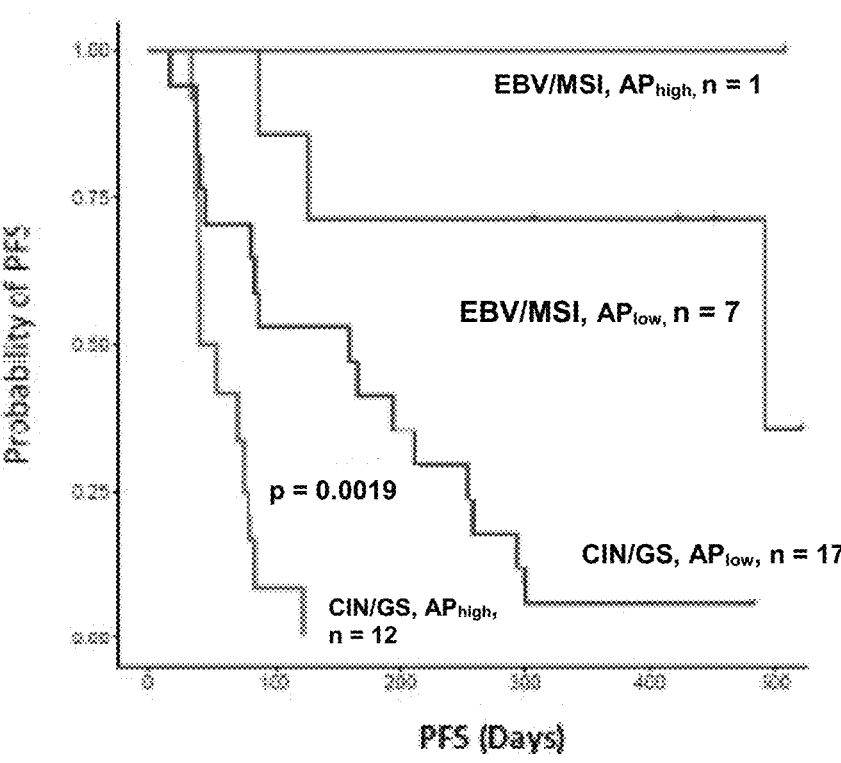

The $AP_{high}$ group had no statistically significant differences in clinicopathological characteristics compared to the $AP_{low}$ group for age, gender or histological subtype. No differences were also detected between the two groups between TCGA subtypes, mutational load, and PDL1 CPS scores (Table 1). The $AP_{low}$ group demonstrated significantly increased expression of CD8A (P=0.0037), GZMA (P=0.0055) and PRF1 (P=0.016) when compared to the $AP_{high}$ group suggesting increased cytotoxic T-cell activity in the $AP_{low}$ group (FIG. 3C). Objective response rate (ORR), defined as either partial or complete response to therapy, was higher in the $AP_{low}$ group compared to $AP_{high}$ group (10/24 vs 1/13, P=0.03) (FIG. 3D). Of note, in the $AP_{high}$ group, the only response was in an MSI subtype tumour. Median progression free survival (PFS) was 55 days in the $AP_{high}$ group compared to 180 days in the $AP_{low}$ group (logrank P=0.0076) (FIG. 4A, 5B). The $AP_{low}$ group had 17% EBV (n=4) and 12% MSI (n=3) TCGA subtype samples, while the $AP_{high}$ group had only 8% MSI (n=1) and no EBV samples (FIG. 4C). As previously shown, PFS between the various TCGA subtypes were different (P=0.0026), with the MSI and EBV subtypes having a significantly longer survival (491 days (MSI/EBV) vs 80 days (CIN/GS)). Notably, amongst the CIN/GS subtype, PFS was also statistically significantly different between the $AP_{low}$ and $AP_{high}$ groups (48 days (CIN/GS $AP_{high}$) vs 161 days (CIN/GS $AP_{low}$), P=0.0019) (FIG. 4D). Based on preliminary overall survival data, a trend towards improved survival was seen in the $AP_{low}$ group (340 days vs 292 days, P=0.16). Multivariate analysis of clinicopathologic and alternate promoter utilization revealed high alternate promoter utilization as an independent predictive factor for PFS with pembrolizumab (HR 0.29, (95% CI 0.099-0.85), P=0.024) (Table 2).

TABLE 1

Differences in characteristics between $AP_{high}$ and $AP_{low}$ groups.

| Characteristics | $AP_{High}$ (n = 13) n (%) | $AP_{Low}$ (n = 24) n (%) | P-value |
|---|---|---|---|
| Age, years | | | |
| <57 | 6 (46) | 11 (46) | 1 |
| ≥57 | 7 (54) | 13 (54) | |
| Gender | | | |
| Male | 11 (85) | 16 (67) | 0.44 |
| Female | 2 (15) | 8 (33) | |
| Primary tumour location | | | |
| Body | 6 (46) | 17 (71) | 0.17 |
| Antrum/Others | 7 (54) | 7 (29) | |
| Histology | | | |
| Poorly differentiated | 5 (38) | 15 (62) | 0.34 |
| Well/Moderately differentiated | 5 (38) | 5 (21) | |
| Signet Ring/Others | 3 (23) | 4 (17) | |
| Immune Signature | | | |
| High | 5 (38) | 14 (58) | 0.31 |
| Low | 8 (62) | 10 (42) | |
| Mesenchymal subtype (ACRG) | | | |
| Non-mesenchymal | 9 (69) | 22 (92) | 0.16 |
| Mesenchymal | 4 (31) | 2 (8) | |

TABLE 1-continued

Differences in characteristics between $AP_{high}$ and $AP_{low}$ groups.

| Characteristics | $AP_{High}$ (n = 13) n (%) | $AP_{Low}$ (n = 24) n (%) | P-value |
|---|---|---|---|
| Mutational load | | | |
| Low | 3 (23) | 13 (54) | 0.13 |
| Moderate | 8 (62) | 7 (29) | |
| High | 2 (15) | 4 (17) | |
| TCGA Subtype | | | |
| CIN | 7 (54) | 6 (25) | 0.26 |
| GS | 5 (38) | 11 (46) | |
| EBV | 0 (0) | 4 (17) | |
| MSI | 1 (8) | 3 (12) | |
| P53 mutation status | | | |
| Mutated | 6 (46) | 17 (71) | 0.17 |
| Wild type | 7 (54) | 7 (29) | |
| KRAS mutation status | | | |
| Mutated | 3 (23) | 4 (17) | 0.68 |
| Wild type | 10 (77) | 20 (83) | |
| PDL1 CPS* | | | |
| 0 | 8 (62) | 6 (29) | 0.22 |
| 1 | 3 (23) | 5 (24) | |
| 2-9 | 0 (0) | 3 (14) | |
| ≥10 | 2 (15) | 7 (33) | |

Fisher test

*3 samples did not have tissue available for PDL1 CPS scoring by immunohistochemistry, all from APlow group.

TABLE 2

Univariate and Multivariate Survival Analysis.

| Variable | Univariate HR (95% CI) | P Value | Multivariate HR (95% CI) | P Value |
|---|---|---|---|---|
| Alternate Promoter Group: High vs Low | 0.36 (0.17-0.78) | 0.0094 | 0.29 (0.099-0.85) | 0.024 |
| TCGA subgroups: CIN/GS vs EBV/MSI | 0.10 (0.024-0.45) | 0.0024 | 0.31 (0.052-1.88) | 0.20 |
| Age | 0.98 (0.95-1) | 0.061 | | |
| Gender: Female vs Male | 1.2 (0.52-2.5) | 0.72 | | |
| Primary tumour site: Body vs Antrum/Others | 0.61 (0.28-1.3) | 0.22 | | |
| Histology Poorly diff/Signet/others vs Well/Mod | 0.98 (0.44-2.2) | 0.97 | | |
| Mutational Load High vs Low/Mod | 5.67 (1.3 24) | 0.018 | 3.46 (0.52-23) | 0.20 |
| P53 mutation status Mutated vs wildtype | 0.74 (0.36-1.56) | 0.43 | | |
| KRAS mutation status Mutated vs wildtype | 2.72 (0.92-7.96) | 0.068 | | |
| Mesenchymal subtype Mesenchymal vs Non-mesenchymal | 0.73 (0.29-1.8) | 0.48 | | |
| Immune Signature High vs Low | 2.31 (1.1-4.8) | 0.025 | 1.82 (0.80-4.12) | 0.15 |
| PDL1 CPS | | | | |
| ≥1 vs 0 | 7.62 (3-19) | <0.001 | 3.09 (1.15-8.29) | 0.025 |

Example 3: Alternate Promoter Utilization Evolution Post-Treatment with Pembrolizumab Paired biopsy samples were available for eight subjects from the second cohort, providing an opportunity to monitor tumour evolution as a consequence of ICI therapeutic pressure. Post-treatment biopsies were taken from the primary stomach tumour at the point of progression on pembrolizumab. Of these eight subjects, two had partial response (PR), with duration of response of 211 and 491 days (both $AP_{low}$), one had stable disease (SD), with duration of response for 167 days ($AP_{low}$), and five had progressive disease (PD) ($AP_{high}$ N=3; $AP_{low}$ N=2) as best response. Interestingly, very consistent shifts were observed in the directionality of alternative promoter utilization based on clinical responses. Specifically, tumours with PR and SD exhibited ×1.5 or higher increase in alternate promoter usage score in the post-treatment biopsy samples compared to pre-treatment biopsy samples, while all five tumours with PD exhibited reductions in alternate promoter usage scores in the post-treatment biopsy sample (Fisher's exact test, P=0.018). These results further support a relationship between alternative promoter landscapes and ICI therapeutic pressure.

Example 4: Alternate Promoter Utilization Across Multiple Tumour Types

To investigate if the applicability of these findings to other tumour types besides gastric cancer, a recently described algorithm was used to infer promoter activity in the Pan-CanAtlas RNA-seq database of 10,393 samples (9668 tumour and 725 normal samples) across 33 tumour types (Table 3). Briefly, using Gencode (release 19) annotations, a set of 113,076 possible promoters was compiled. Promoter activity was inferred by quantifying the expression initiated at each promoter using unique junctional reads, assuming that isoforms with identical or very close TSSs are regulated by the same promoter.

TABLE 3

TCGA cohort description and sample size.

| Tumour type | TCGA code | Tumour samples (n) | Normal samples (n) | Tumour + normal (n) |
|---|---|---|---|---|
| Adrenocortical carcinoma | ACC | 79 | 0 | 79 |
| Bladder Urothelial Carcinoma | BLCA | 405 | 19 | 424 |
| Breast invasive carcinoma | BRCA | 1095 | 112 | 1207 |
| Cervical squamous cell carcinoma and endocervical adenocarcinoma | CESC | 306 | 3 | 309 |
| Cholangiocarcinoma | CHOL | 36 | 9 | 45 |
| Colon adenocarcinoma | COAD | 281 | 41 | 322 |
| Diffuse Large B-cell Lymphoma | DLBC | 48 | 0 | 48 |
| Esophageal carcinoma | ESCA | 185 | 11 | 196 |
| Glioblastoma multiforme | GBM | 165 | 5 | 170 |
| Head and Neck squamous cell carcinoma | HNSC | 504 | 44 | 548 |
| Kidney Chromophobe | KICH | 66 | 25 | 91 |
| Kidney renal clear cell carcinoma | KIRC | 530 | 72 | 602 |
| Kidney renal papillary cell carcinoma | KIRP | 291 | 32 | 323 |
| Acute Myeloid Leukemia | LAML | 171 | 0 | 171 |
| Brain Lower Grade Glioma | LGG | 528 | 0 | 528 |
| Liver hepatocellular carcinoma | LIHC | 373 | 50 | 423 |
| Lung adenocarcinoma | LUAD | 506 | 59 | 565 |
| Lung squamous cell carcinoma | LUSC | 500 | 51 | 551 |
| Mesothelioma | MESO | 87 | 0 | 87 |

TABLE 3-continued

TCGA cohort description and sample size.

| Tumour type | TCGA code | Tumour samples (n) | Normal samples (n) | Tumour + normal (n) |
|---|---|---|---|---|
| Ovarian serous cystadenocarcinoma | OV | 307 | 0 | 307 |
| Pancreatic adenocarcinoma | PAAD | 179 | 4 | 183 |
| Pheochromocytoma and Paraganglioma | PCPG | 184 | 3 | 187 |
| Prostate adenocarcinoma | PRAD | 498 | 52 | 550 |
| Rectum adenocarcinoma | READ | 95 | 10 | 105 |
| Sarcoma | SARC | 263 | 2 | 265 |
| Skin Cutaneous Melanoma | SKCM | 472 | 1 | 473 |
| Stomach adenocarcinoma | STAD | 415 | 35 | 450 |
| Testicular Germ Cell Tumours | TGCT | 156 | 0 | 156 |
| Thyroid carcinoma | THCA | 509 | 59 | 568 |
| Thymoma | THYM | 120 | 2 | 122 |
| Uterine Corpus Endometrial Carcinoma | UCEC | 177 | 24 | 201 |
| Uterine Carcinosarcoma | UCS | 57 | 0 | 57 |
| Uveal Melanoma | UVM | 80 | 0 | 80 |
| Combined | | 9668 | 725 | 10393 |

Figure 5:
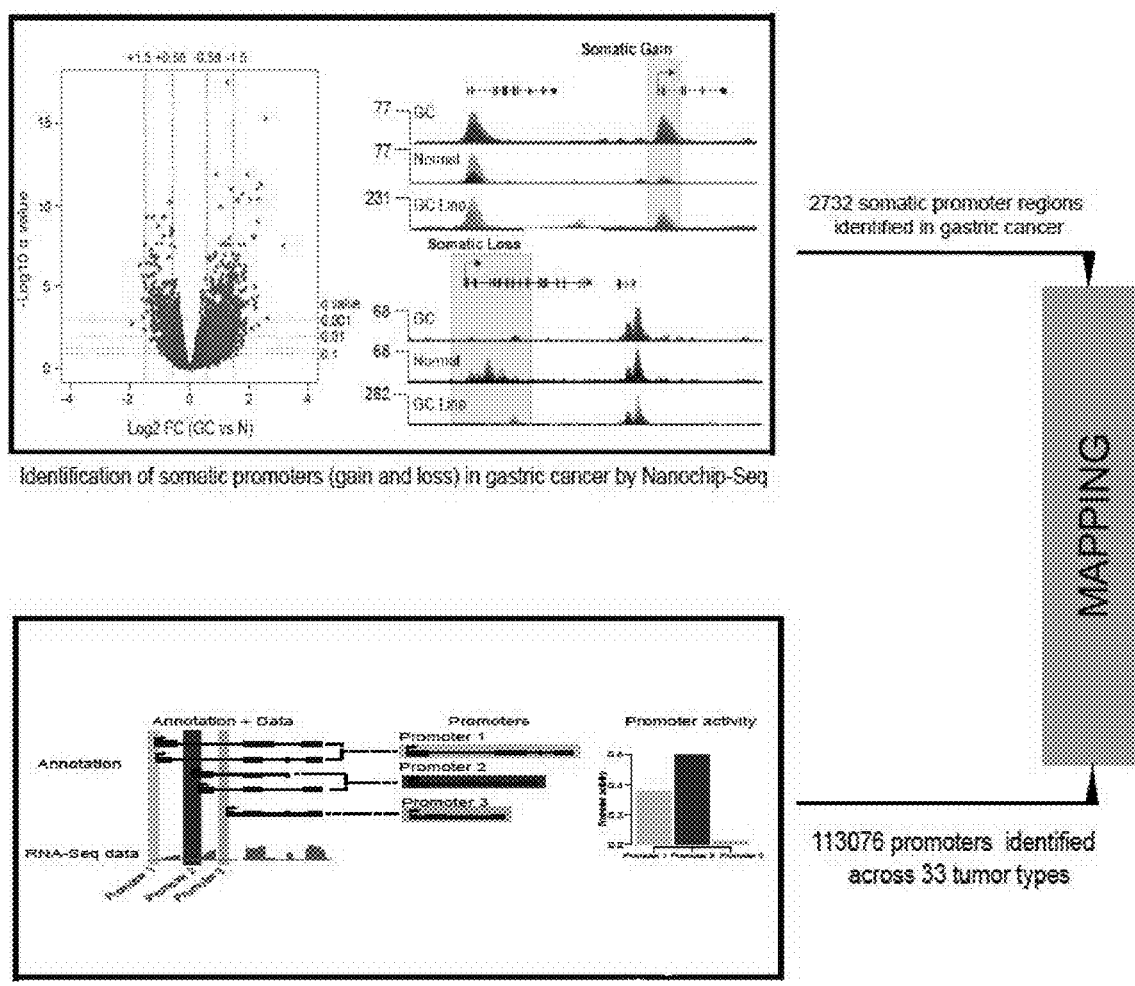
FIG. 5 shows the bioinformatics workflow for APBscore algorithm. Somatic promoter regions (gain and loss) identified in gastric cancer (2732 regions) are mapped against all promoters identified in Pan-Cancer analysis from TCGA (113,076 promoters). In total, 4672 promoters were selected, and relative promoter activity used for calculation of APB-score. Tumours are dichotomized into $APB_{high}$ and $APB_{low}$ at the $80^{th}$ centile of APBscore.
Figure 5:
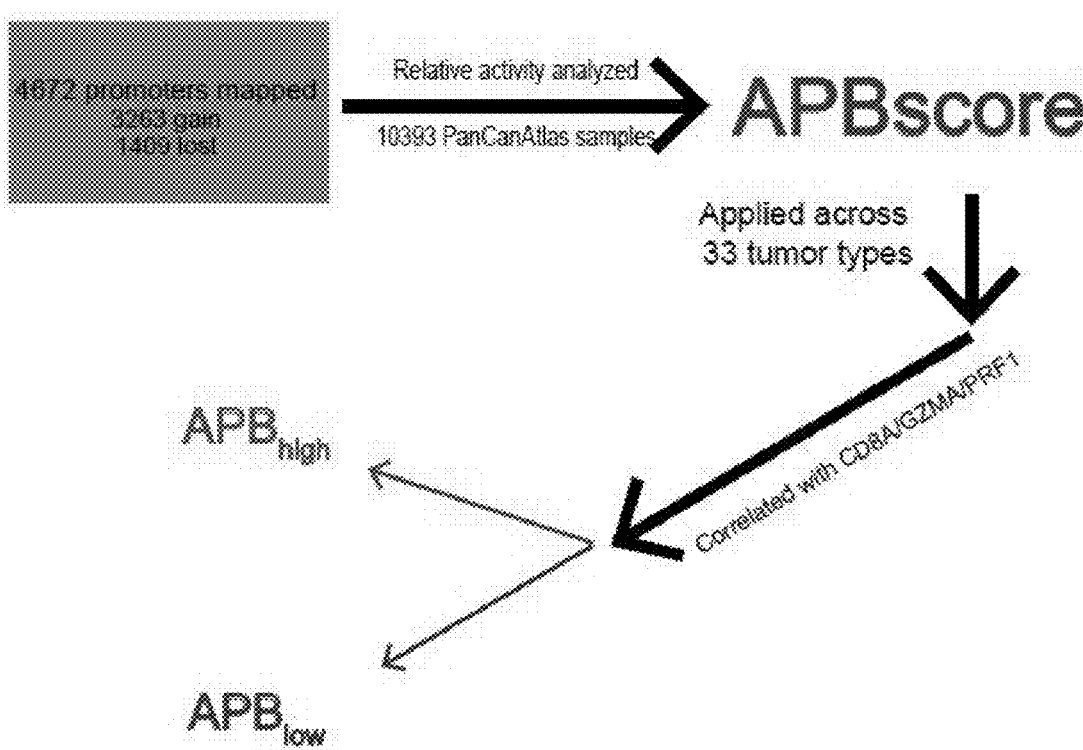

Of the 113,076 promoters, 4672 promoters mapped to 2732 tumour-associated promoter regions previously defined in gastric cancer. It was hypothesized that alterations in this set of promoters might represent a generalized pan-tumour response to host immune recognition, not limited to gastric cancer. To test this hypothesis, the 4672 promoters were used to compute APB levels (APBscore) for each tumour (FIG. 5). As shown in FIG. 1, a wide range of APBscores were observed both within and between tumour types. The median APBscore was 178 for the entire cohort (range: 46 to 241). Tumour types with the lowest median APBscores included thyroid cancer (THCA) (median 165, range: 54 to 207), diffuse large B cell lymphoma (DLBC) (median: 166, range: 108 to 196) and lung adenocarcinoma (LUAD) (median: 167, range: 141 to 215). In contrast, glioblastoma (GBM) (median: 207, range: 172 to 241), low grade glioma (LGG) (median: 204, range: 130 to 230) and testicular germ cell tumours (TGCT) (median: 189, range: 83 to 218) had the highest median APBscores.

Figure 6A:
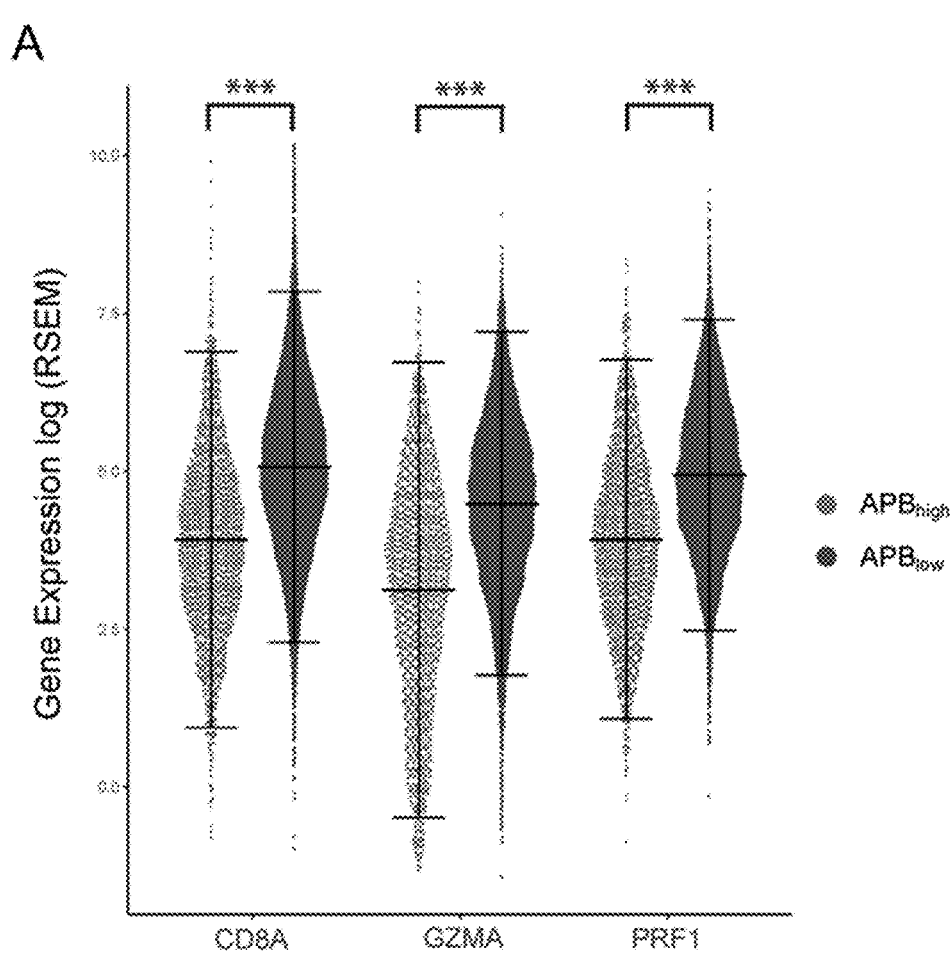
FIG. 6 shows the correlation of APBscore groups with markers of cytolytic T-cell activity. In particular, (A) shows the association between $APB_{high}$ group vs $APB_{low}$ group (all tumour samples, pan-cancer) with T-cell immune correlates. Tumours were dichotomized into $APB_{high}$ and $APB_{low}$ at the $80^{th}$ centile of APBscore. $APB_{high}$ group are in light grey (placed on the left side for each marker), whereas those in $APB_{low}$ group are in dark grey (placed on the right side for each marker). Depicted are the expression of T-cell markers CD8A and the T-cell cytolytic markers GZMA and PRF1. $APB_{high}$ group shows lower expression of immune markers (Wilcoxon test p<0.0001 (*) for CD8A, GZMA and PRF1). (B) shows the association between $APB_{high}$ group vs $APB_{low}$ group with CD8A, GZMA and PRF1 for select tumour types: bladder cancer (BLCA), breast cancer (BRCA), cervical squamous cell carcinoma (CESC), esophageal carcinoma (ESCA), head and neck squamous cell carcinoma (HNSC), liver hepatocellular carcinoma (LIHC), lung squamous cell carcinoma (LUSC), ovarian cancer (OV) and stomach adenocarincoma (STAD). $APB_{high}$ group are in light grey (placed on the left side for each marker), whereas those in $APB_{low}$ group are in dark grey (placed on the right side for each marker). (*=p<0.0001, **=p<0.001, *=p<0.01, NS=p>0.05, Wilcoxon test).
Figure 6B:
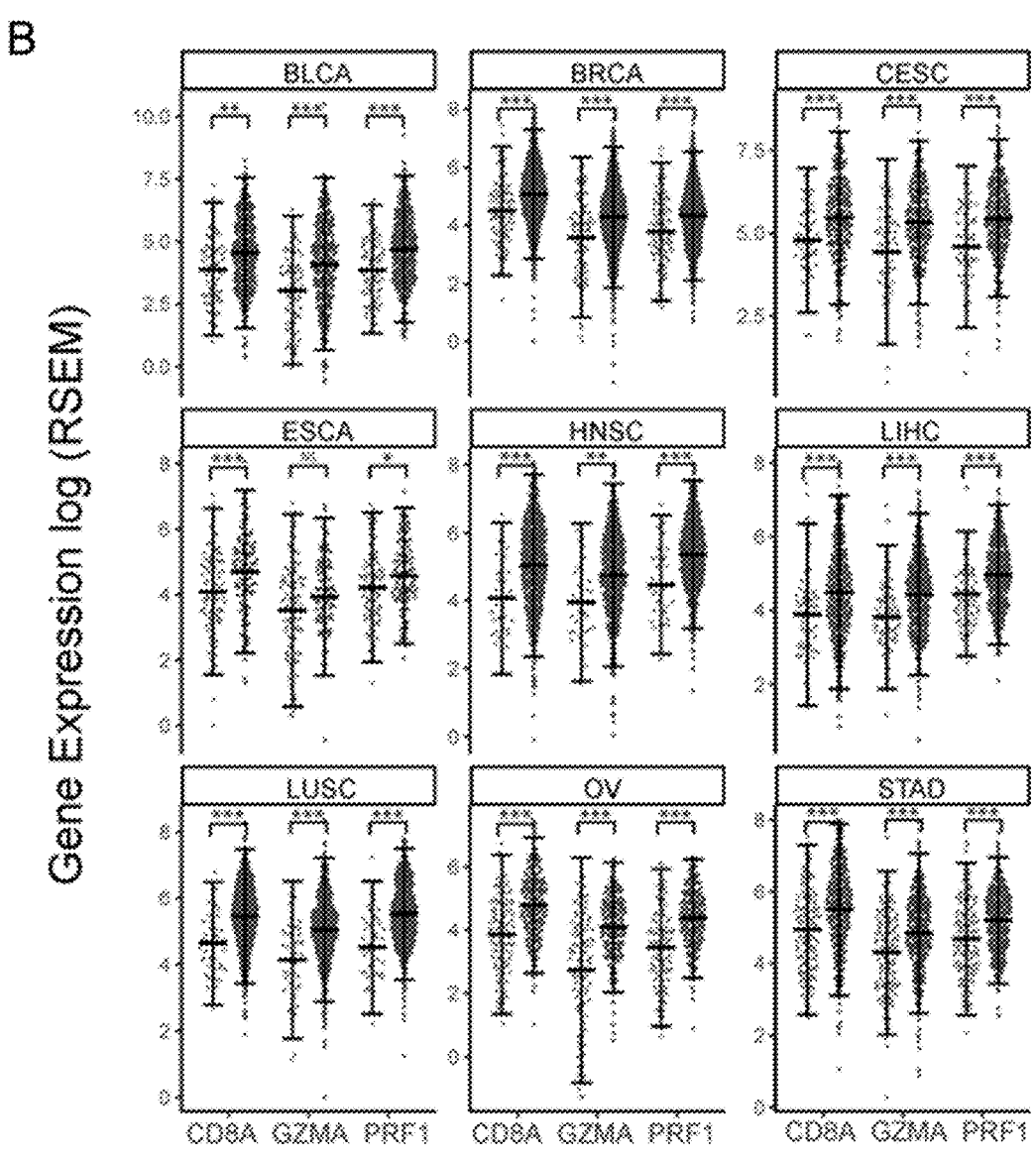

Tumour APBscores were correlated with markers of T-cell cytolytic activity: CD8A, GZMA and PRF1. Similar to other pan-cancer TCGA studies, the primary analyses were conducted on the entire cohort of TCGA samples agnostic of tumour-type, but tumour-type specific results were also provided. Previously, it was observed that dichotomizing tumours at the median or top tertile yielded significant correlations with CD8A, GZMA and PRF1. However, as these studies were done with smaller sample sizes, it was opted to re-establish the ideal cut-off for dichotomizing tumours, with respect to correlation with these three genes. APBscore thresholds were thus tested at various centiles ($10^{th}$, $20^{th}$, $30^{th}$ . . . , $90^{th}$) to dichotomize the $APB_{high}$ and $APB_{low}$ groups. For the entire cohort (all tumour types), at all nine cut-offs for dichotomy, $APB_{high}$ tumours had significantly lower levels of CD8A, GZMA and PRF1 compared to $APB_{low}$ tumours (p<0.0001) (FIG. 6A). The $80^{th}$ centile was found to have the strongest correlation with the three genes, with 19 out 33 tumour types correlating significantly with CD8A, GZMA and PRF1. For subsequent analysis, tumours were dichotomized into the $APB_{high}$ and $APB_{low}$ groups at the $80^{th}$ centile (APBscore cutoff: 190) of the entire cohort. Importantly, previous findings in stomach cancer (STAD) were robustly replicated in this analysis, even using a different technique for interrogating alternate promoters (FIG. 6B). To address potential confounding by tumour-type, a tumour-type specific analysis was also conducted, where each tumour-type was dichotomized into $APB_{high}$ and $APB_{low}$ groups at the median APBscore of that specific tumour type. For 20 of the 33 tumour types, there was significant correlation with CD8A, GZMA and PRF1. Eight tumour types did not have a significant correlation at any cut-off: kidney chromophobe (KICH), DLBC, thymoma and thymic carcinoma (THYM), kidney renal cell cancer (KIRC), acute myeloid leukemia (LAML), cholangiocarcinoma (CHOL), uterine carcinoma sarcoma (UCS), pheochromocytoma and paraganglioma (PCPG). Of these eight, CHOL, KICH and UCS have relatively small sample sizes (n<100), while DLBC, THYM, LAML are of hematologic/immune origin.

Notably, compared to the set of 4672 promoters originally defined in gastric cancer used to define APBscore, similar strengths of correlation to CD8A/GZMA/PRF1 expression were not observed if APBscore was inferred using all 113,076 identified promoters, or other similarly sized promoter subsets obtained from permutation testing (empirical p<0.001). This observation supports the hypothesis that although the APBscore was originally derived from gastric cancer, the APBscore algorithm may apply across multiple tumour types possibly reflecting a conserved pan-cancer response to host immunity. To investigate specific functions of the tumour-associated promoter isoforms, 570 promoters (12% of 4672) upregulated in at least 100 tumours (~1% of cohort of 9668 tumours) were analyzed. Different tumour types utilized specific clusters of promoter isoforms, and network analysis of gene functions revealed that alternate promoters affect genes with diverse roles. This may suggest that on a genome-wide scale, alternate promoter selection in tumours may be driven less by intrinsic gene function and more by extrinsic selective pressures (e.g. host anti-tumour immunity). Tumour APBscores were also compared to non-malignant tissues. Of 725 matched normal tissue samples analyzed in the PanCanAtlas, only 5% (n=36 normal samples) were classified as $APB_{high}$ (at the $80^{th}$ centile cut-off). When normal and tumour samples were clustered by alternate promoter usage, normal samples clustered close to, but distinct from their corresponding tumour type. In 15 out of the 16 tumour types with at least 10 normal samples, tumour samples were more likely to be classified as $APB_{high}$ compared to normal samples (Fisher's exact, p<0.001).

Example 5: Alternate Promoter Utilization Between Tumor and Normal Samples

Figure 7:
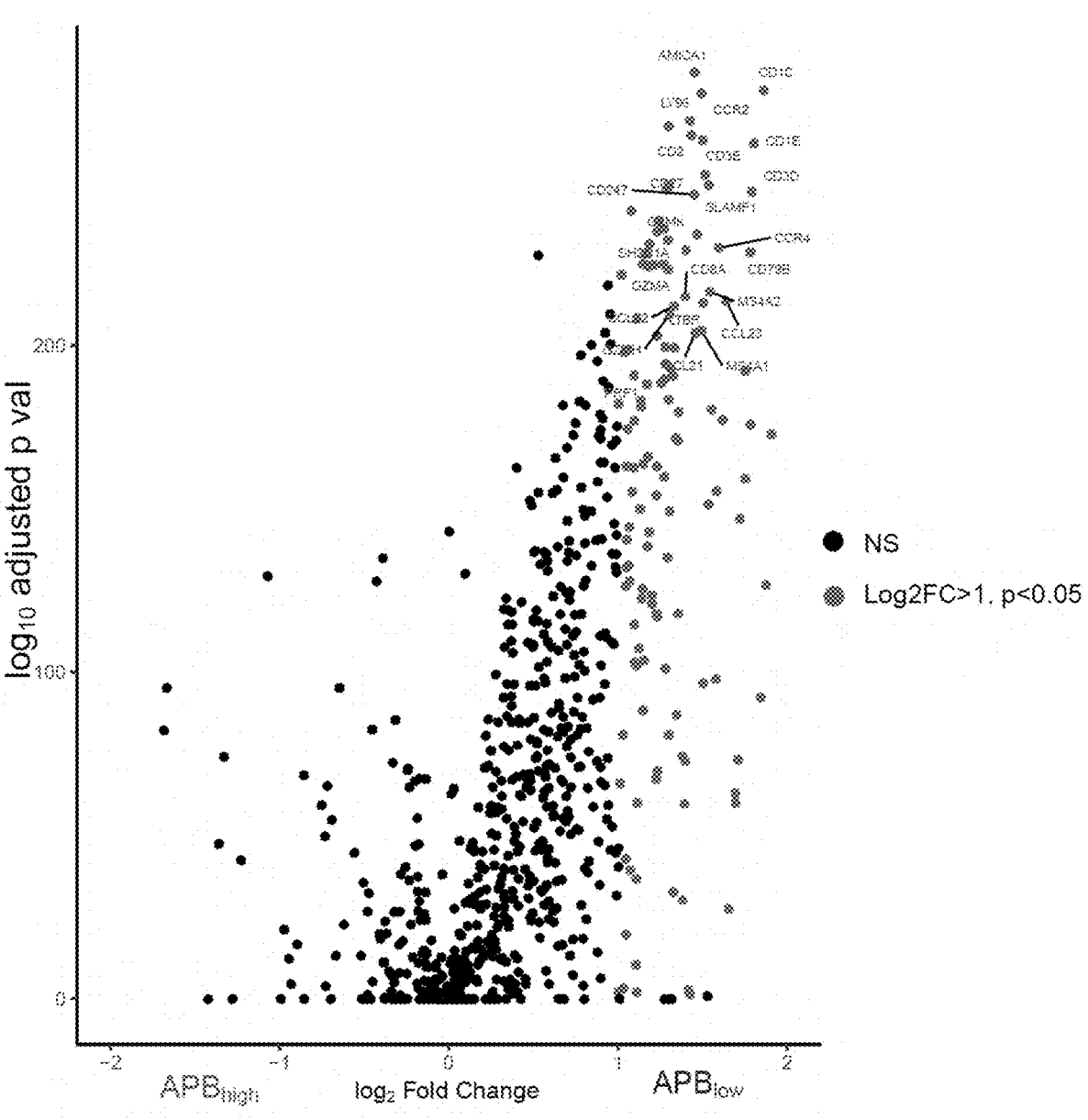
FIG. 7 shows the differential gene expression in APBscore groups highlighting immune genes. In this volcano plot of immune genes correlated with $APB_{high}$ and $APB_{low}$, the x-axis is the $\log_2$ fold change ($\log_2$FC) of gene expression (RSEM) between $APB_{high}$ and $APB_{low}$. The y-axis is the $-\log_{10}$ adjusted p-value results (Bonferroni correction). Significant genes defined as $\log_2$FC>1 and adjusted p value <0.05 are expressed as red dots. The top genes ($\log_2$FC>1.3 and $-\log_{10}$ adjusted p value >200) are labelled.
Figure 8:
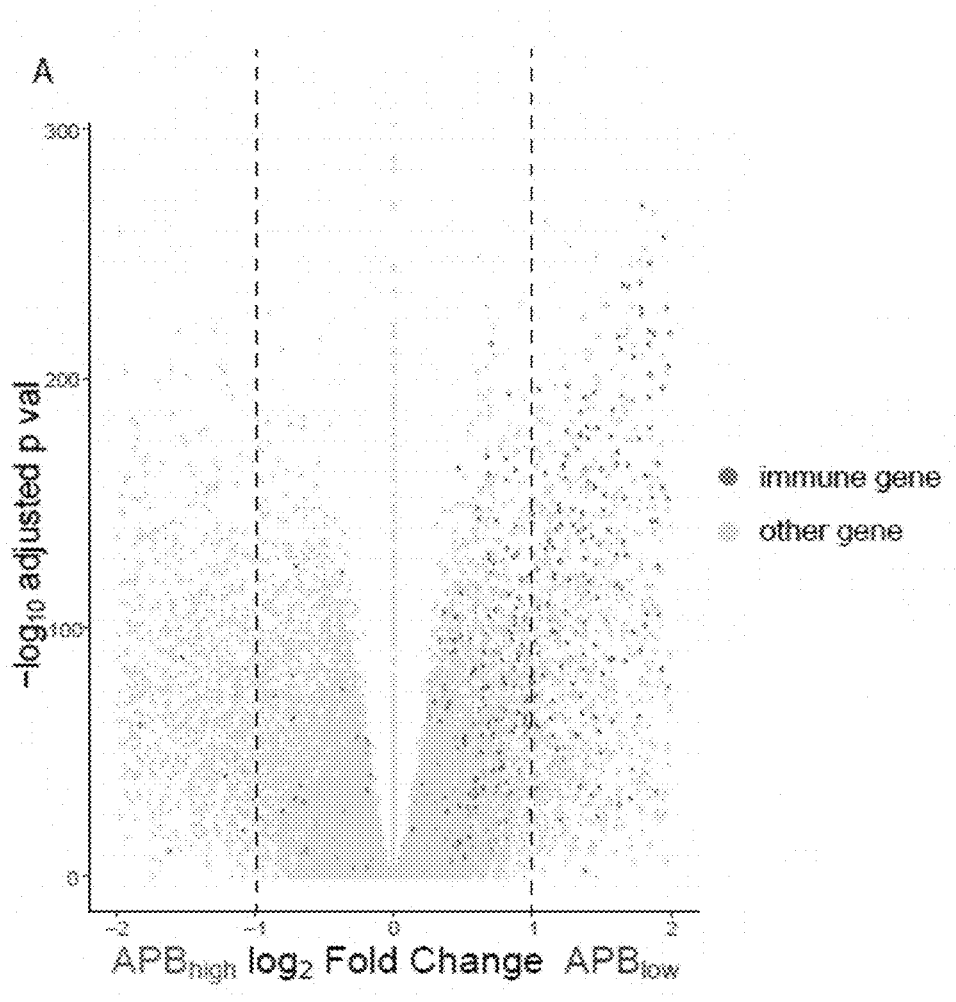
FIG. 8 shows the association between APBscore groups and other immune-correlates. In particular, the figure shows a volcano plot of ~20,000 genes in the PanCanAtlas correlated with $APB_{high}$ and $APB_{low}$. The x-axis is the $\log_2$ fold change ($\log_2$FC) of gene expression (RSEM) between $APB_{high}$ and $APB_{low}$. The y-axis is the $-\log_{10}$ adjusted p-value results (Bonferroni correction). Immune genes are expressed as red dots. Equal split of overall gene expression is seen between both groups, with a skew of under-expression of immune genes in the $APB_{high}$ group.
Figure 9:
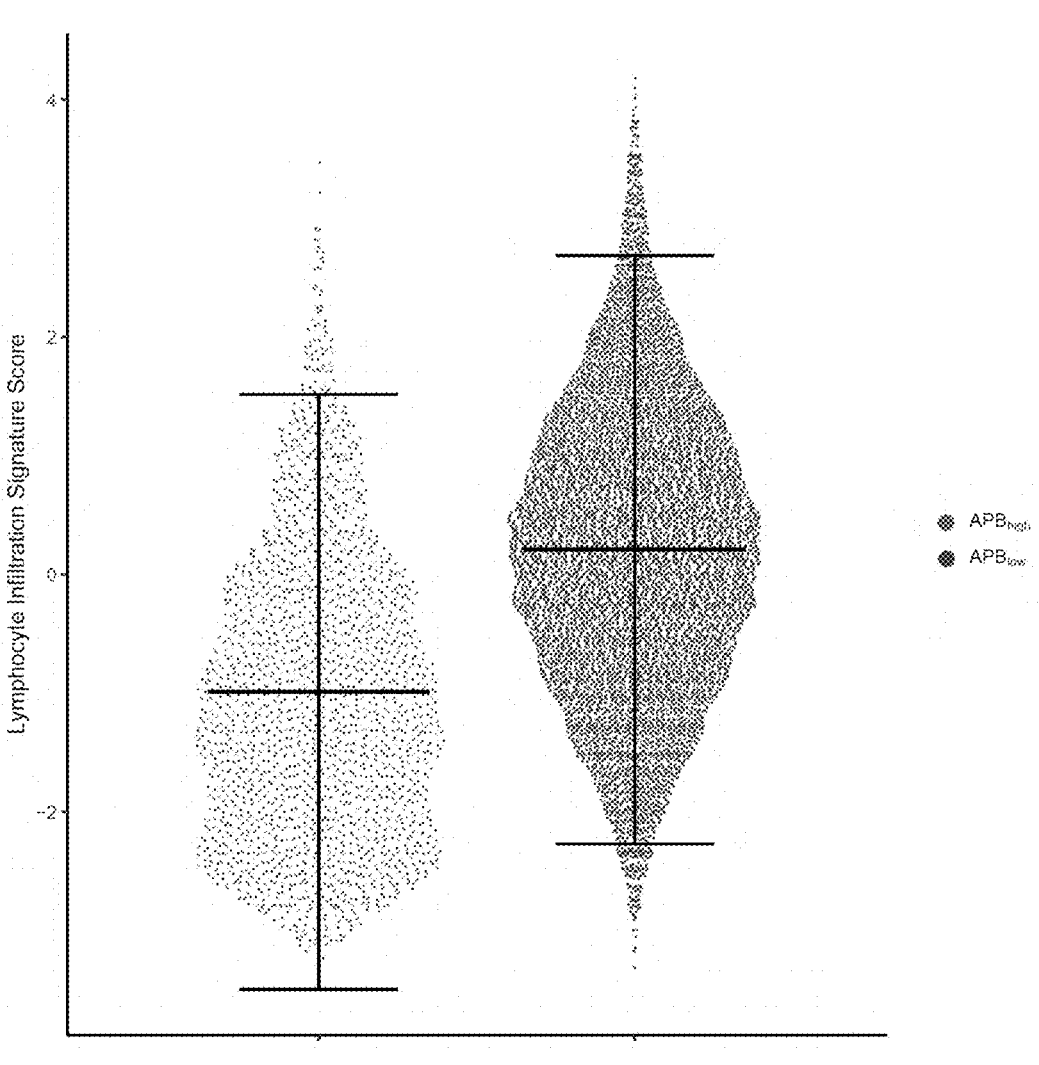
FIG. 9 shows the correlation of lymphocyte infiltration signature score with APBscore. The lymphocyte infiltration signature is dichotomized by APBscore groups. The $APB_{low}$ group has a statistically higher score compared to $APB_{high}$ (Wilcoxon test p<0.0001).
Figure 10:
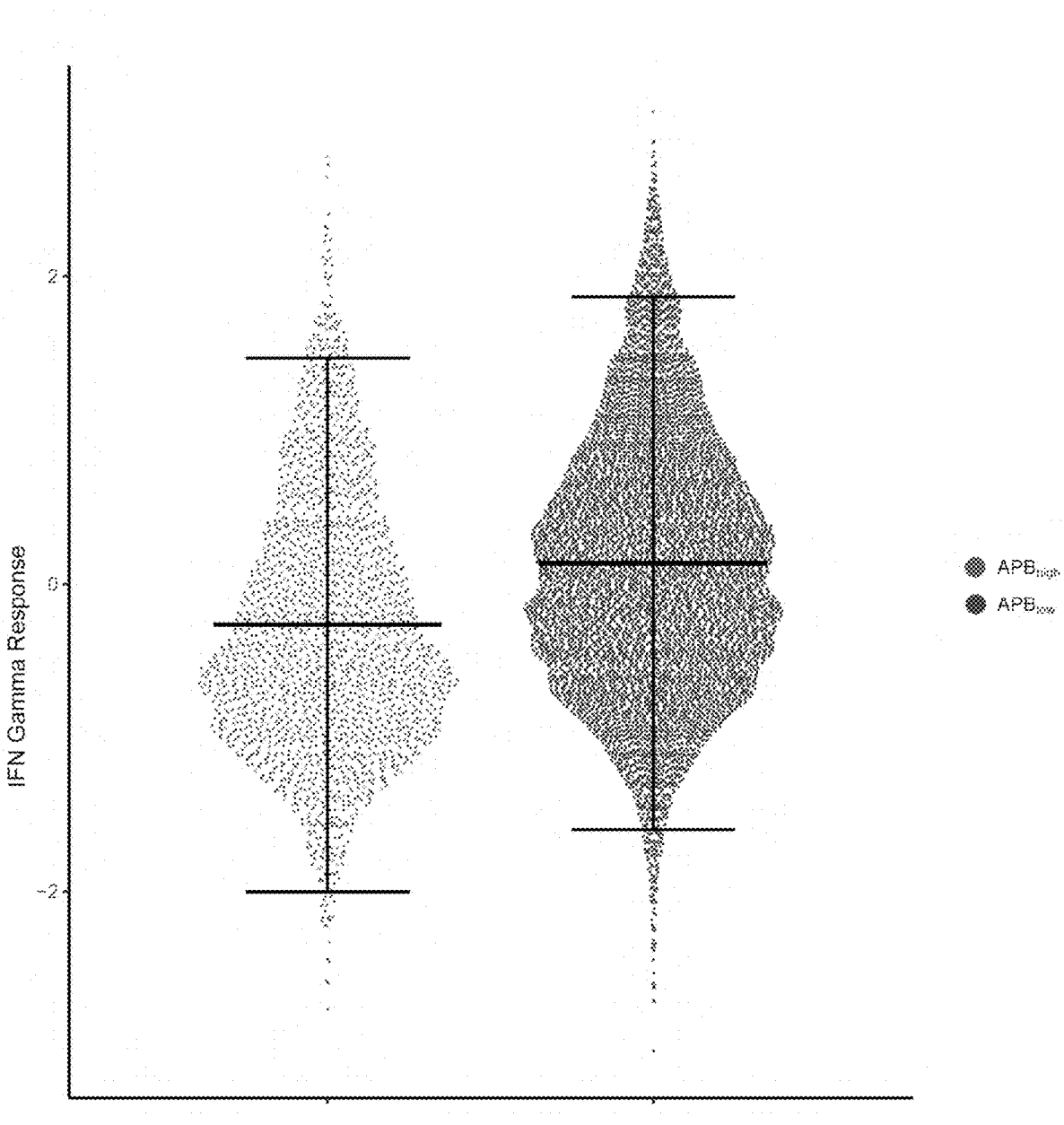
FIG. 10 shows the correlation of IFN-γ response signature with APBscore. The IFN-γ response signature as defined by dichotomized by APBscore groups. The $APB_{low}$ group has a statistically higher score compared to $APB_{high}$ (Wilcoxon test p<0.0001).

To further explore interactions between alternate promoter utilization and tumour immunity, the analyses were expanded to study relationships between APBscore and a broad spectrum of ~700 immune-related genes covering multiple immune cell types, immune checkpoints and antigens. The majority of these genes (78%) exhibited significantly higher expression in $APB_{low}$ tumours compared to $APB_{high}$ tumours (FIG. 7), suggesting that that $APB_{high}$ tumours have an immune-depleted phenotype. Differential expression analysis of all ~20,000 genes available in the PanCanAtlas confirmed that the down-regulation of genes in the $APB_{high}$ subgroup was restricted to only the immune genes (FIG. 8A). In a Pan-Cancer immune landscape study using TGCA samples, tumours were classified into six immune subtypes characterized by distinct immune signatures-wound healing, IFN-γ dominant, inflammatory, lymphocyte depleted, immunologically quiet, and TGF-β dominant. When APBscore was correlated with these immune subtypes, it was found that lymphocyte depleted or immunologically quiet subtypes were more likely to be $APB_{high}$ tumours (Fisher's exact p<0.0001) (FIG. 8B). Notably, lymphocyte depleted $APB_{high}$ tumours comprised a diversity of tumour subtypes, while immunologically quiet $APB_{high}$ tumours were largely dominated by LGGs. In contrast, IFN-γ and inflammatory subtypes were more likely to be $APB_{low}$ tumours (Fisher's exact p<0.0001) (FIG. 8B), and $APB_{low}$ tumours were also more likely to have higher lymphocyte infiltration signature scores and IFN-γ response signatures (p<0.0001, Wilcoxon test) (FIG. 9, FIG. 10). Importantly, APBscores were uncorrelated with TMB levels (r=0.02, p=0.02), suggesting distinct processes drive alternate promoter utilization and the acquisition of DNA somatic mutations.

Example 6: Alternate Promoter Utilization and Survival Outcomes

The association between APBscores with progression-free survival (PFS) and overall survival (OS) data obtained from the TCGA Pan-Cancer analysis was investigated. To avoid confounding at the pan-cancer level where survival outcomes may be influenced by intrinsic tissue- or site-specific properties, individual tumour-type specific analyses were conducted. When analysed at the tumour type-specific level, the majority of tumour types did not exhibit any correlations between APBscore and PFS or OS. Only a few tumour types exhibited survival differences between the APB groups (KIRC, LGG, LUAD, THYM). Multivariate analysis of APBscore and disease subtype also suggests that APBscore is not an independent prognostic predictor of survival for patients who have not undergone ICI therapy.

Example 7: Alternate Promoter Utilization and Pembrolizumab Resistance

Figure 11:
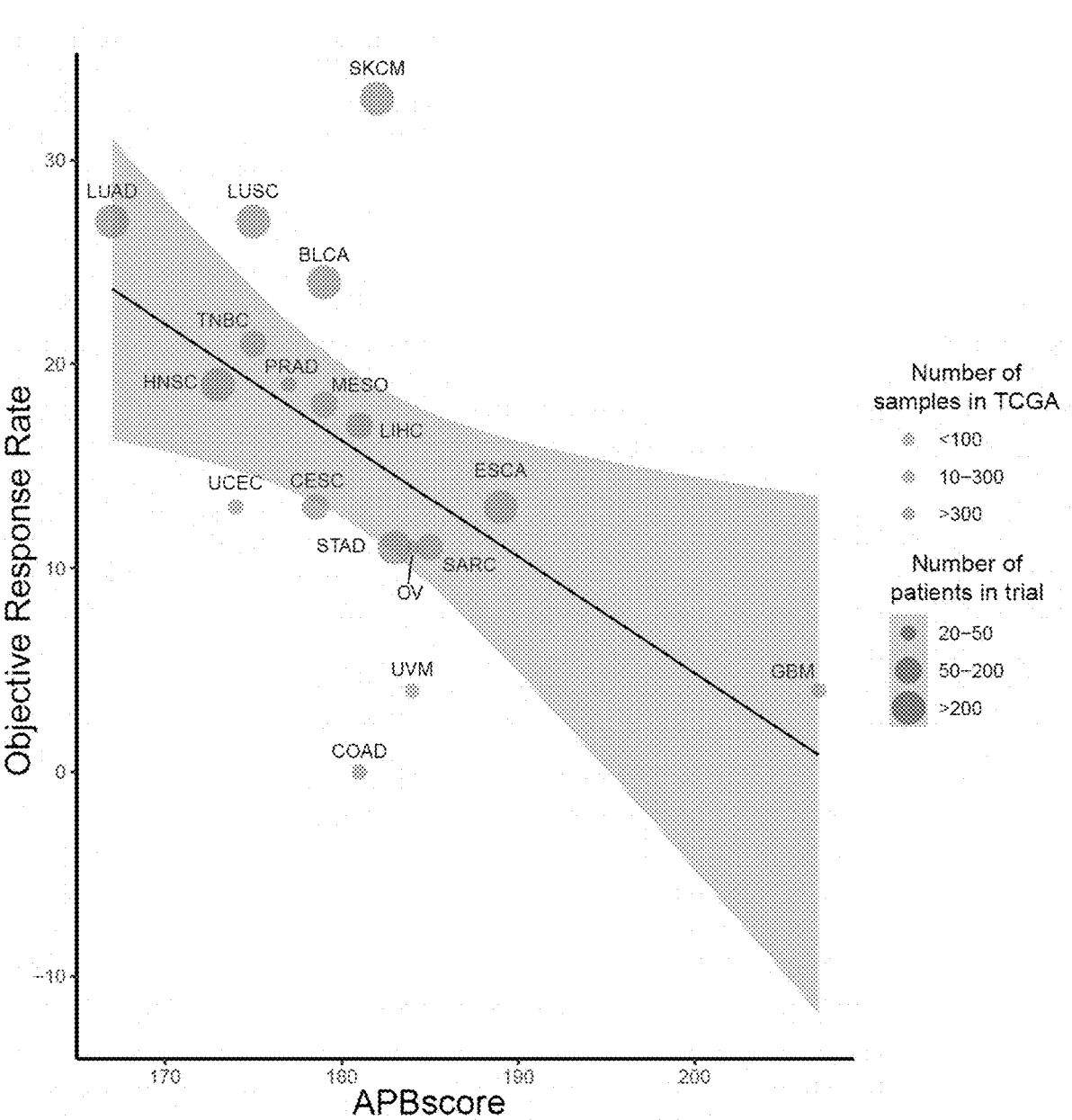
FIG. 11 shows the correlation between APBscore and objective response rates (ORR) with pembrolizumab in 19 tumour types selected due to correlation with CD8A, GZMA and PRF1. The x-axis is the median APBscore per tumour type and the y-axis is the ORR of the tumour type with single-agent pembrolizumab as described in published trials.

To test if $APB_{high}$ tumours are more resistant to ICIs as previously shown in metastatic gastric cancer, the association of APBscore with objective response rates (ORRs) for pembrolizumab reported in independent studies were quantified. Across all the tumour types, a significant negative correlation between ORR and APBscore (Pearson's R=−0.46, p=0.025) was observed. Similar correlations were not observed with CD8A (r=0.18, p=0.4), GZMA (r=0.17, p=0.4), or PRF1 (r=0.3, p=0.1). Consistent with previous studies, positive associations were observed with TMB (r=0.53, p=0.0078) and PD-L1 expression (r=0.42, r=0.042). These results thus suggest that APBscore and TMB are likely complementary in identifying distinct subsets of tumours, with TMB selecting types with better ICI response, and APBscore identifying those with lack of response since APBscore and TMB are not correlated. Interestingly, when only tumour types exhibiting significant APBscore correlations with CD8A, GZMA and PRF1 were selected for the analysis (19 tumour types), the correlations between APBscore and ORRs improved in strength and significance: Pearson's R=−0.55, p=0.019 (FIG. 11). Taken collectively, these results extend previous findings shown in gastric cancer and establish a pan-cancer relationship between APBscore and pembrolizumab resistance.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A method of identifying a patient suffering from cancer as benefiting or not benefiting from immune checkpoint inhibition (ICI) therapy comprising the steps of:

a) measuring an expression level of one or more preselected markers in a cancerous biological sample obtained from the patient, wherein the preselected marker is a marker that is associated with a somatic promoter region in a cancerous biological sample;

b) identifying a differentially expressed alternative promoter based on the expression level of the one or more preselected markers measured in step (a) relative to a non-cancerous biological sample, wherein an increase in the expression level of the one or more preselected markers in the cancerous biological sample compared to the expression level of the non-cancerous sample for a gained promoter indicates a differentially expressed alternative promoter, and wherein a decrease in the expression level of the one or more preselected markers in the cancerous biological sample compared to the expression level of the non-cancerous sample for a lost promoter indicates a differentially expressed alternative promoter;

c) calculating an alternative promoter usage score by determining the sum of the number of gained promoters with at least a 4-fold increase in the expression level of transcripts and the number of lost promoters with an expression level lower than 0.25-fold when compared to the median expression level of transcripts;

d) identifying the patient as benefiting or not benefiting from ICI therapy using the alternative promoter usage score by comparing the alternative promoter usage score calculated in step (c) with a reference score to identify the patient as benefiting or not benefiting from ICI therapy, wherein an increased alternative promoter usage score compared to the reference score identifies the patient as not benefiting from ICI therapy and wherein a decreased alternative promoter usage score compared to the reference score identifies the patient as benefiting from ICI therapy, wherein the reference score is the 66th or 80th percentile of alternative promoter usage scores from one or more non-cancerous biological samples; and e) treating the patient identified as benefiting from ICI therapy with an ICI therapy.

2. The method of claim 1, wherein the preselected marker is a nucleic acid molecule or a peptide.

3. The method of claim 1, wherein the gained promoter is a promoter that is gained or increased in a cancerous biological sample compared to a non-cancerous biological sample and wherein the lost promoter is a promoter that is lost or decreased in a cancerous biological sample compared to a non-cancerous biological sample.

4. The method of claim 1, wherein the expression level of the one or more preselected markers in the cancerous biological sample is compared with a percentile expression level of said one or more preselected markers in the one or more non-cancerous biological samples, or the mean expression level of said one or more preselected markers in the one or more non-cancerous biological samples, or both.

5. The method of claim 1, wherein the increased alternative promoter usage score is a score above the $66^{th}$ or $80^{th}$ percentile of alternative promoter usage scores from one or more reference samples, and wherein the decreased alternative promoter usage score is a score below the $66^{th}$ or $80^{th}$ percentile of alternative promoter usage scores from one or more reference samples.

*  *  *  *  *